US010813926B2

(12) United States Patent
Graham et al.

(10) Patent No.: US 10,813,926 B2
(45) Date of Patent: *Oct. 27, 2020

(54) MORPHINAN COMPOUNDS

(71) Applicant: Concert Pharmaceuticals, Inc., Lexington, MA (US)

(72) Inventors: Philip B. Graham, Boston, MA (US); I. Robert Silverman, Arlington, VA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/523,920

(22) Filed: Jul. 26, 2019

(65) Prior Publication Data

US 2020/0022975 A1 Jan. 23, 2020

Related U.S. Application Data

(63) Continuation of application No. 16/036,164, filed on Jul. 16, 2018, now Pat. No. 10,406,155, which is a continuation of application No. 15/488,064, filed on Apr. 14, 2017, now Pat. No. 10,022,370, which is a continuation of application No. 15/148,568, filed on May 6, 2016, now Pat. No. 9,655,895, which is a continuation of application No. 14/726,758, filed on Jun. 1, 2015, now Pat. No. 9,340,512, which is a continuation of application No. 14/546,173, filed on Nov. 18, 2014, now Pat. No. 9,266,837, which is a continuation of application No. 14/208,968, filed on Mar. 13, 2014, now Pat. No. 8,916,582, which is a continuation of application No. 13/119,905, filed as application No. PCT/US2009/057476 on Sep. 18, 2009, now Pat. No. 8,710,072.

(60) Provisional application No. 61/098,511, filed on Sep. 19, 2008.

(51) Int. Cl.
| A61K 31/485 | (2006.01) |
| C07D 221/28 | (2006.01) |
| A61P 25/08 | (2006.01) |
| A61P 25/16 | (2006.01) |
| A61P 29/00 | (2006.01) |
| C07B 59/00 | (2006.01) |
| C07D 471/08 | (2006.01) |
| A61K 45/06 | (2006.01) |
| A61K 31/195 | (2006.01) |
| A61K 31/4709 | (2006.01) |

(52) U.S. Cl.
CPC .......... *A61K 31/485* (2013.01); *A61K 31/195* (2013.01); *A61K 31/4709* (2013.01); *A61K 45/06* (2013.01); *A61P 25/08* (2018.01); *A61P 25/16* (2018.01); *A61P 29/00* (2018.01); *C07B 59/002* (2013.01); *C07D 221/28* (2013.01); *C07D 471/08* (2013.01)

(58) Field of Classification Search
CPC ............................ A61K 31/485; C07D 221/28
USPC ..................................... 514/289, 299; 546/74
See application file for complete search history.

(56) References Cited

U.S. PATENT DOCUMENTS

| 6,221,335 B1 | 4/2001 | Foster |
| 6,440,710 B1 | 8/2002 | Keinan et al. |
| 6,603,008 B1 | 8/2003 | Ando et al. |
| 7,501,433 B2 | 3/2009 | Wu et al. |
| 7,517,990 B2 | 4/2009 | Ito et al. |
| 7,973,049 B2 | 7/2011 | Tung |
| 8,710,072 B2 | 4/2014 | Graham et al. |
| 8,916,582 B2 | 12/2014 | Graham et al. |
| 9,266,837 B2 | 2/2016 | Graham et al. |
| 9,340,512 B2 * | 5/2016 | Graham ................... A61P 25/08 |
| 9,655,895 B2 * | 5/2017 | Graham ............... C07D 221/28 |
| 10,022,370 B2 * | 7/2018 | Graham ................... A61P 25/08 |
| 10,406,155 B2 * | 9/2019 | Graham ............. A61K 31/4709 |
| 2007/0082929 A1 | 4/2007 | Gant et al. |
| 2007/0197695 A1 | 8/2007 | Potyen et al. |
| 2008/0103122 A1 | 5/2008 | Veltri |
| 2018/0243289 A1 | 8/2018 | Tung |
| 2018/0243290 A1 | 8/2018 | Tung |
| 2018/0243291 A1 | 8/2018 | Tung |
| 2019/0038618 A1 | 2/2019 | Graham et al. |

FOREIGN PATENT DOCUMENTS

| CN | 1968697 | 5/2007 |
| EP | 2334678 | 6/2011 |
| WO | WO 1995/26325 | 10/1995 |

(Continued)

OTHER PUBLICATIONS

Albayrak et al., "Beneficial Effects of the Sigma-1 Agonist Fluvoxamine for Tardive Dyskinesia in Patients with Postpsychotic Depressive Disorder of Schizophrenia: Report of 5 Cases," Prim Care Companion CNS Disord., Nov. 2012, retrieved on Sep. 21, 2015, http://www.ncbi.nlm.nig.gov/pmc/articles/PMC3622527/?report=printable, 8 pages.

(Continued)

*Primary Examiner* — Niloofar Rahmani

(74) *Attorney, Agent, or Firm* — Fish & Richardson P.C.

(57) ABSTRACT

This invention relates to novel morphinan compounds and pharmaceutically acceptable salts thereof. This invention also provides compositions comprising a compound of this invention and the use of such compositions in methods of treating diseases and conditions that are beneficially treated by administering a $\sigma_1$ receptor agonist that also has NMDA antagonist activity.

22 Claims, 3 Drawing Sheets

(56) References Cited

FOREIGN PATENT DOCUMENTS

| WO | WO 2003/097608 | 11/2003 |
|---|---|---|
| WO | WO 2004/006930 | 1/2004 |
| WO | WO 2005/110412 | 11/2005 |
| WO | WO 2007/092329 | 8/2007 |
| WO | WO 2007/118651 | 10/2007 |
| WO | WO 2008/137474 | 11/2008 |

OTHER PUBLICATIONS

Baillie et al., "The Use of Stable Isotopes in Pharmacological Research," Pharmacology Rev, 1981, 33(2):81-132.

Belleau et al., "Clastic Binding on the Opiate Receptor," J. Med Chem., 17(8): 908-909 (1974).

Blake et al. "Studies with Deuterated Drugs," J. of Pharma. Sciences, 1975, 64(3):367-391.

Bölcskei et al., "Synthesis of Deuterated Dextromethorphan Derivatives," Arkivoc, 3: 182-193 (2008).

Bonnet et al., "Nonmotor symptoms in Parkinson's Disease in 2012: Relevant Clinical Aspects", Hindawi Pub Corp, vol. 2012, pp. 1-15, 2012.

Browne et al., "Stable Isotope Techniques in Early Drug Development: An Economic Evaluation," J. Clin. Pharmacology, 1998, 38: 213-20.

Cherrah et al., "Study of Deuterium Isotope Effects on Protein Binding by Gas Chromatography/Mass Spectrometry. Caffeine and Deuterated Isotopomers," Biomed and Environmental Mass Spectrometry, 1987, 14: 653-57.

Chinese Office Action in CN Application No. 200980142670.4, dated Nov. 23, 2012, 14 pages (w/ English translation).

Chou et al., "Dimemorfan N-demethylation by mouse liver microsomal cytochrome P450 enzymes," Life Sciences, 77: 735-745 (2005).

Chou et al., "The oxidative metabolism of dimemorfan by human cytochrome P450 enzymes." J. of Pharma. Sciences, pp. 1-15 (2009).

Crottes et al., "The sigma-1 receptor: a regulator of cancer cell electrical plasticity?," Frontiers in Physiology, Jul. 2013, 4(175):1-10.

"Dastosin Syrup," Prospectus, 4 pages (2007).

"Dastosin," Patient Information Leaflet, Ministry of Health Social Politics and Equality (Spanish version and English translation), (2002).

Dermer, "Another anniversary for the war on cancer," Bio/Technology, 1994, 12:320.

Dyck et al., "Effects of Deuterium Substitution on the Catabolism of β-Phenylethylamine: An In Vivo Study," J. Neurochemistry, 1986, 46:399-404.

Eurasian Search Report, in Eurasian Application No. 201690033, dated May 10, 2016, 3 pages.

Extended European Search Report in European Application No. 11188848.3-2117, dated Dec. 23, 2011, 8 pages.

Extended European Search Report in European Application No. 17179704.6-1462, dated Sep. 7, 2017, 8 pages.

Final Office Action dated Feb. 19, 2013 in U.S. Appl. No. 13/155,827, filed Jun. 8, 2011, CIP of U.S. Appl. No. 13/119,905, presently under examination.

Fisher et al., "The complexities inherent in attempts to decrease drug clearance by blocking sites of CYP-mediated metabolism," Curr. Opin. Drug Discov. Dev., 2006, 9(1):101-109.

Ford et al., "Neuropsychiatric aspects of dementia," Maturitas, Elsevier, 2014, 79:209-215.

Foster et al., "Deuterium isotope effects in studies of drug metabolism," Trends in Pharmaceutical Sciences, 1984, 5:524-527.

Foster et al., "Deuterium Isotope Effects in the Metabolism of Drugs and Xenobiotics: Implications for Drug Design," Adv. Drug Res., 1985, 14: 2-40.

Freshney et al., "Culture of Animal Cells: A manual of basic technique," John Wiley and Sons, 2005, 5th edition, 7 pages.

Fukuto et al., "Determination of the Mechanism of Demethylenation of (Methylenedioxy)phenyl Compounds by Cytochrome P450 Using Deuterium Isotope Effects," J. Med. Chem., 1991, 34:2871-2876.

Furuse et al., "Sigma-1 receptor agonist fluvoxamine for delirium in intensive care units: report of five cases," Annals of General Psychiatry, 2010, 9:18, 4 pages.

Gouyette et al., "Synthesis of Deuterium-labelled Elliptinium and its Use in Metabolic Studies," Biomed. and Environmental Mass Spectrometry, 1988, 15: 243-47.

Hashimoto et al., "Activation of sigma-1 receptor chaperone in the treatment of neuropsychiatric diseases and its clinical implication," J. Pharmacological Sciences, 2015, 127:6-9.

Haskins et al., "The Application of Stable Isotopes in Biomedical Research," Biomed. Spectrometry, 1982, 9(7):269-77.

Honma et al., "The Metabolism of Roxatidine Acetate Hydrochloride," Drug Metab. Dispos, 1987, 15(4): 551-559.

Ida et al., "The nonnarcotic Antitussive Drug Dimemorfan: A Review," Clinical Therapeutics, 19(2): 215-231 (1997).

International Preliminary Report on Patentability for PCT/US2009/057476, dated Mar. 31, 2011, 7 pages.

International Search Report and Written Opinion for PCT/US2009/057476, dated Nov. 12, 2009, 12 pages.

Japanese Office Action in Japanese Application No. 2015-078415, dated Feb. 2, 2016, 8 pages [with English translation].

Kigoshi et al., "Effect of Several d-Morphinans on Ascites Tumors in Mice," Japan J. Pharmacol., 1987,44:293-302.

Kushner et al. "Pharmacological uses and perspectives of heavy water and deuterated compounds," Can. J. Physiol. Pharmacol. 1999, 77: 79-88.

Lu et al., "Dose Response Effects of C-10068 on Attenuation of Nonconvulsive Seizures Induced by Penetrating-Ballistic-like Brain Injury in Rats," WR AIR, 2012, 1 page.

Magnus et al., "Nonepileptic uses of gabapentin," Epilepsia, 1999, 40:S66-S72.

Martin et al., "The Sigma Receptor Ligand (+)-Pentazocine Prevents Apoptotic Retinal Ganglion Cell Death Induced in vitro by Homocysteine and Glutamate," Brain Res Mol Brain Res, Apr. 2004, 123:66-75.

Morganroth et al., "Comparative Study of Encainide and Quinidine in the Treatment of Ventricular Arrhythmias," JACC, 1986, 7:9-16.

Murakami et al., "Studies on Morphian Derivatives. II. 1) The Synthesis of d-3-Methyl-N-methylmorphinan, a New Antitussive," Chem Pharm Bull., 1972, 20(8):1706-1710.

Newman et al., "Synthesis and Evaluation of 3-Substituted 17-Methylmorphinan Analogs as Potential Anticonvulsant Agents," J. Med. Chem., 35: 4135-4142 (1992).

Nieto et al., "Role of Sigma-1 Receptors in Paclitaxel-Induced Neuropathic Pain in Mice," J. Pain, 2012, 13(11):1107-1121.

Nishimura et al., "Potentiation of Nerve Growth Factor-Induced Neurite Outgrowth by Fluvoxamine: Role of Sigma-1 Receptors, IP3 Receptors and Cellular Signaling Pathways," PloS One, Jul. 20008, 3(7):e2558, 9 pages.

Non-final Office Action dated Jun. 29, 2012 in U.S. Appl. No. 13/155,827, filed Jun. 8, 2011, CIP of U.S. Appl. No. 13/119,905, presently under examination.

Office Action in Japanese App. No. 2011-527994 dated Mar. 4, 2014, 10 pages [with English translation].

Patent Prosecution File History of EP Application No. EP 2334678, EPO-Espacenet, retrieved on Jan. 13, 2014, 41 pages.

Pieniaszek et al., "Moricizine bioavailability via simultaneous, dual, stable isotope administrations: bioequivalence," J. Clin. Pharmacology, 1999, 39:817-25.

Response to Non-final Office Action filed Dec. 28, 2012 in U.S. Appl. No. 13/155,827, filed Jun. 8, 2011, CIP of U.S. Appl. No. 13/119,905, presently under examination.

Shin et al., "The dextromethorphan analog dimemorfan attenuates kainite-induced seizures via σl receptor activation: comparison with the effects of dextromethorphan," British Journal of Pharmacology, 2005, 144:908-918.

Smith et al., "In Vivo Protection against Retinal Neurodegeneration by Sigma Receptor 1 Ligand (+)-Pentazocine," Invest Ophthalmol Vis Sci, Sep. 2008, 49(9):4154-4161.

(56) References Cited

OTHER PUBLICATIONS

Supplemental Response to Non-final Office Action filed Jan. 4, 2013 in U.S. Appl. No. 13/155,827, filed Jun. 8, 2011, CIP of U.S. Appl. No. 13/119,905, presently under examination.

Tonn et al., "Simultaneous Analysis of Diphenhydramine and a Stable Isotope Analog ($^2$H10) Diphenhydramine Using Capillary Gas Chromatography with Mass Selective Detection in Biological Fluids from Chronically Instrumented Pregnant Ewes," Biol. Mass Spectrometry, 1993, 22:633-642.

Tortella et al., "Novel Anticonvulsant Analogs of Dextromethorphan: Improved Efficacy, Potency, Duration and Side-Effect Profile," J. Pharmacology and Experimental Therapeutics, 1994, 268(2):727-733.

Watson et al., "Controlled Release oxycodone relieves neuropathic pain: a randomized controlled trial in painful diabetic neuropathy," Pain, 2003, 105:71-78.

Werling et al., "A comparison of the binding profiles of dextromethorphan, memantine, fluoxetine and amitriptyline: Treatment of involuntary emotional expression disorder," Exp. Neurol., 2007, 207:248-257.

Wolen et al., "The Application of Stable Isotopes to Studies of Drug Bioavailability and Bioequivalence," J. Clin. Pharmacology, 1986, 26:419-424.

\* cited by examiner

MORPHINAN COMPOUNDS

CROSS-REFERENCE TO RELATED APPLICATIONS

This application is a continuation of U.S. patent application Ser. No. 16/036,164, filed Jul. 16, 2018, which is a continuation of U.S. patent application Ser. No. 15/488,064, filed Apr. 14, 2017 (now U.S. Pat. No. 10,022,370), which is a continuation of U.S. patent application Ser. No. 15/148,568, filed May 6, 2016 (now U.S. Pat. No. 9,655,895), which is a continuation of U.S. patent application Ser. No. 14/726,758, filed Jun. 1, 2015 (now U.S. Pat. No. 9,340,512), which is a continuation of U.S. patent application Ser. No. 14/546,173, filed Nov. 18, 2014 (now U.S. Pat. No. 9,266,837), which is a continuation of U.S. patent application Ser. No. 14/208,968, filed Mar. 13, 2014 (now U.S. Pat. No. 8,916,582), which is a continuation of U.S. patent application Ser. No. 13/119,905, filed Jul. 1, 2011 (now U.S. Pat. No. 8,710,072), which is a National Stage application under 35 U.S.C. § 371 of International Application No. PCT/US2009/057476, filed Sep. 18, 2009, which claims priority to U.S. Provisional Application Ser. No. 61/098,511, filed Sep. 19, 2008, all of which are incorporated by reference herein in their entireties.

TECHNICAL FIELD

This invention relates to novel morphinan compounds and pharmaceutically acceptable salts thereof. This invention also provides compositions comprising a compound of this invention and the use of such compositions in methods of treating diseases and conditions that are beneficially treated by administering a sigma-1 receptor agonist that also has NMDA antagonist activity.

BACKGROUND

Dextromethorphan, also known by its chemical name (+)-3-methoxy-17-methyl-(9α,13α,14α)-morphinan, is currently one of the most widely used antitussives.

In addition to the physiological activity noted above, dextromethorphan is also an agonist of the σ2 receptor, an N-methyl-D-aspartate (NMDA) antagonist, and an α3β4 nicotinic receptor antagonist. Dextromethorphan inhibits neurotransmitters, such as glutamate, from activating receptors in the brain. Uptake of dopamine and serotonin are also inhibited.

Dextromethorphan is approved for use in over the counter cough suppressant products. It is currently in Phase I clinical trials for treating subjects with voice spasms, and Phase III clinical studies for treating Rett Syndrome (http://www.clinicaltrials.gov). Dextromethorphan is being studied with other drugs in a Phase II clinical trial characterizing pain processing mechanisms in subjects with irritable bowel syndrome (http://www.clinicaltrials.gov/). Dextromethorphan is also in Phase I clinical trials for treating hyperalgesia in methadone-maintained subjects (http://www.clinicaltrials.gov/).

In addition, a combination of dextromethorphan hydrobromide and quinidine sulfate is currently in Phase III clinical trials for treating diabetic neuropathic pain (http://www.clinicaltrials.gov). This drug combination, also know as Zenvia®, is in Phase III clinical trials for treating Involuntary Emotional Expression Disorder (IEED), also known as pseudobulbar affect, in subjects suffering from Alzheimer's disease, stroke, Parkinson's disease and traumatic brain injury (http://www.clinicaltrials.gov).

Dextromethorphan is metabolized in the liver. Degradation begins with O- and N-demethylation to form primary metabolites dextrorphan and 3-methoxy-morphinan, both of which are further N- and O-demethylated respectively to 3-hydroxy-morphinan. These three metabolites are believed to be therapeutically active. A major metabolic catalyst is the cytochrome P450 enzyme 2D6 (CYP2D6), which is responsible for the O-demethylation reactions of dextromethorphan and 3-methoxymorphinan. N-demethylation of dextromethorphan and dextrorphan are catalyzed by enzymes in the related CYP3A family. Conjugates of dextrorphan and 3-hydroxymorphinan can be detected in human plasma and urine within hours of its ingestion.

Dextromethorphan abuse has been linked to its active metabolite, dextrorphan. The PCP-like effects attributed to dextromethorphan are more reliably produced by dextrorphan and thus abuse potential in humans may be attributable to dextromethorphan metabolism to dextrorphan. (Miller, S C et al., Addict Biol, 2005, 10(4): 325-7., Nicholson, K L et al., Psychopharmacology (Berl), 1999 Sep. 1, 146(1): 49-59., Pender, E S et al., Pediatr Emerg Care, 1991, 7: 163-7). One study on the psychotropic effects of dextromethorphan found that people who are extensive metabolizers (EM's) reported a greater abuse potential compared to poor metabolizers (PM's) providing evidence that dextrorphan contributes to dextromethorphan abuse potential (Zawertailo L A, et al., J Clin Psychopharmacol, 1998 August, 18(4): 332-7).

A significant fraction of the population has a functional deficiency in the CYP2D6 enzyme. Thus, because the major metabolic pathway for dextromethorphan requires CYP2D6, the decreased activity results in much greater duration of action and greater drug effects in CYP2D6-deficient subjects. In addition to intrinsic functional deficiency, certain medications, such as antidepressants, are potent inhibitors of the CYP2D6 enzyme. With its slower metabolism in some people, dextromethorphan, especially in combination with other medication(s), can lead to serious adverse events.

A longer than recommended duration of a drug in the body may provide continued beneficial effects, but it may also create or prolong undesired side effects. Undesirable side effects at recommended doses of dextromethorphan therapy include nausea, loss of appetite, diarrhea, drowsiness, dizziness, and impotence.

Dimemorfan, an analog of dextromethorphan, also known by its chemical name as (+)-(9α,13α,14α)-3,17-dimethyl-morphinan, is a non-narcotic antitussive. The antitussive activity of dimemorfan is believed to result from direct action on the cough center in the medulla (Ida, H., Clin Ther., 1997, March-April; 19(2): 215-31).

In addition to its antitussive properties, dimemorfan has been shown to have anticonvulsant and neuroprotective effects possibly arising from N-methyl-D-aspartate (NMDA) antagonism of dextromethorphan (DM) and/or high-affinity DM σ receptors (Chou, Y-C. et al., Brain Res., 1999, Mar. 13; 821(2): 516-9). Activation at the σ-1 receptor has been found to provide anticonvulsant action in rats and mice, like DM, but without the behavioral side effects produced by DM and its metabolite, dextrorphan (Shin, E. J. et al., Br J Pharmacol., 2005, April; 144(7): 908-18 and Shin, E. J. et al., Behavioural Brain Research, 2004, 151: 267-276).

Metabolism of dimemorfan in humans is known to proceed through cytochrome P450 catalyzed N-demethylation as well as 3-methyl oxidation. Greater than 98% of a dose of dimemorfan is metabolized in healthy human males and none of the metabolites have been shown to have antitussive effects (Chou Y-C., et al., Life Sci., 2005, Jul. 1; 77(7): 735-45 and Chou Y-C., et al., J Pharm Sci., 2009, July: 1-15).

Additionally, two ether analogs of dextromethorphan, [(+)-3-ethoxy-17-methylmorphinan] also referred to herein as "dextroethorphan," and [(+)-3-(2-propoxy)-17-methylmorphinan] also referred to herein as "dextroisopropor-phan," have shown anticonvulsant activity (Newman, A. et al., J Med Chem., 1992, 35(22): 4135-42 and Tortella, F. et al., J Pharmacol and Exp Therap., 1994, 268(2): 727-733) as well as neuroprotective effects in rats (Tortella, F. et al., Neurosci. Lett., 1995, 198(2): 79-82).

Accordingly, it is desirable to provide new compounds that have the beneficial activities of dextromethorphan, dimemorfan, dextroethorphan and dextroisoproporphan and may also have other benefits, e.g., reduced adverse side effects, with a decreased metabolic liability to further extend its pharmacological effective life, enhance subject compliance and, potentially, to decrease population pharmacokinetic variability and/or decrease its potential for dangerous drug-drug interactions or decrease the likelihood of dextromethorphan abuse due to the formation of untoward metabolites such as dextrorphan.

SUMMARY

Provided herein is a compound of Formula I:

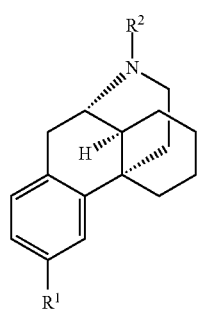

(I)

or a pharmaceutically acceptable salt thereof, wherein:

$R^1$ is selected from —O—$(C_2-C_4)$alkyl and —$(C_1-C_4)$ alkyl, wherein $R^1$ is optionally substituted with one or more deuterium atoms; and $R^2$ is selected from $CH_3$, $CH_2D$, $CHD_2$, and $CD_3$;

provided that at least one deuterium atom is present at either $R^1$ or $R^2$.

In some embodiments, $R^2$ is $CH_3$ or $CD_3$. In some embodiments, $R^1$ is —O—$CH_2CH_3$, —O—$CD_2CD_3$, —O—$CD_2CH_3$, —O—$CH_2CD_3$, —O—$CH(CH_3)_2$, —O—$CD(CD_3)_2$, —O—$CH(CD_3)_2$, —O—$CD(CH_3)_2$, —O—$CH_2CH(CH_3)_2$, —O—$CD_2CH(CH_3)_2$, —O—$CH_2CD(CH_3)_2$, —O—$CH_2CH(CD_3)_2$, —O—$CD_2CD(CH_3)_2$, —O—$CD_2CH(CD_3)_2$, —O—$CH_2CD(CD_3)_2$, or —O—$CD_2CD(CD_3)_2$.

In some embodiments $R^1$ is —O—$(C_2-C_4)$alkyl substituted with one or more deuterium atoms.

In some embodiments, $R^1$ is —O—$CD_2CD_3$, —O—$CD_2CH_3$, —O—$CH_2CD_3$, —O—$CD(CD_3)_2$, —O—$CH(CD_3)_2$, —O—$CD(CH_3)_2$, —O—$CD_2CH(CH_3)_2$, —O—$CH_2CD(CH_3)_2$, —O—$CH_2CH(CD_3)_2$, —O—$CD_2CD(CH_3)_2$, —O—$CD_2CH(CD_3)_2$, —O—$CH_2CD(CD_3)_2$, or —O—$CD_2CD(CD_3)_2$.

In some embodiments, $R^1$ is —O—$CD_2CD_3$, —O—$CD_2CH_3$, —O—$CH_2CD_3$, —O—$CD(CD_3)_2$, —O—$CH(CD_3)_2$, or —O—$CD(CH_3)_2$.

In some embodiments, $R^1$ is —O—$CD_2CD_3$ or —O—$CD(CD_3)_2$.

In some embodiments, $R^1$ is —O—$CD(CD_3)_2$.

In some embodiments, a Formula I compound is selected from any one of the compounds in Table 1 set forth below:

| Compound No. | $R^1$ | $R^2$ |
|---|---|---|
| 100 | —O—$CD_2CD_3$ | $CD_3$ |
| 101 | —O—$CD_2CH_3$ | $CD_3$ |
| 102 | —O—$CD(CD_3)_2$ | $CD_3$ |
| 103 | —O—$CD(CH_3)_2$ | $CD_3$ |
| 104 | —O—$CD_2CD_3$ | $CH_3$ |
| 105 | —O—$CD_2CH_3$ | $CH_3$ |
| 106 | —O—$CD(CD_3)_2$ | $CH_3$ |
| 107 | —O—$CD(CH_3)_2$ | $CH_3$ |

In some embodiments of the compound of Formula 1, $R^1$ is —$(C_1-C_4)$alkyl which is optionally substituted with one or more deuterium atoms. In some of these embodiments, $R^2$ is $CH_3$ or $CD_3$. In some of these embodiments, $R^1$ is —$CH_3$, —$CD_3$, —$CH_2CH_3$, —$CD_2CD_3$, —$CD_2CH_3$, —$CH_2CD_3$, —$CH(CH_3)_2$, —$CD(CD_3)_2$, —$CH(CD_3)_2$, —$CD(CH_3)_2$, —$CH_2CH(CH_3)_2$, —$CD_2CH(CH_3)_2$, —$CH_2CD(CH_3)_2$, —$CH_2CH(CD_3)_2$, —$CD_2CD(CH_3)_2$, —$CD_2CH(CD_3)_2$, —$CH_2CD(CD_3)_2$, or —$CD_2CD(CD_3)_2$. In some of these embodiments, $R^1$ is —$CD_3$, —$CD_2CD_3$, —$CD_2CH_3$, —$CH_2CD_3$, —$CD(CD_3)_2$, —$CH(CD_3)_2$, —$CD(CH_3)_2$, —$CD_2CH(CH_3)_2$, —$CH_2CD(CH_3)_2$, —$CH_2CH(CD_3)_2$, —$CD_2CD(CH_3)_2$, —$CD_2CH(CD_3)_2$, —$CH_2CD(CD_3)_2$, or —$CD_2CD(CD_3)_2$. In some of these embodiments, $R^1$ is —$CD_3$, —$CD_2CD_3$, or —$CD_2CD(CD_3)_2$. In some of these embodiments, $R^1$ is —$CD_3$. In some of these embodiments, $R^1$ is —$CH_3$, —$CH_2CH_3$, —$CH(CH_3)_2$, or —$CH_2CH(CH_3)_2$ and $R^2$ is selected from $CD_3$.

In some embodiments, the compound of Formula I is selected from any one of:

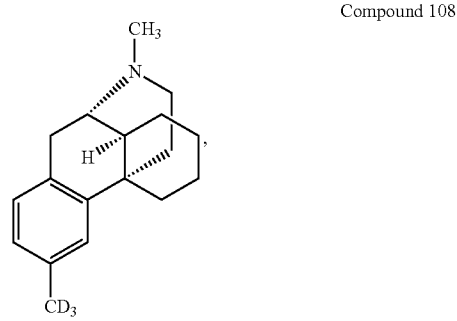

Compound 108

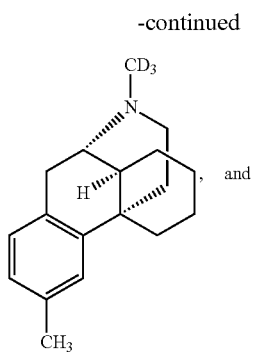

Compound 109 and

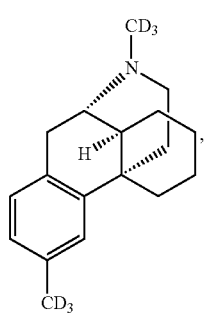

Compound 110

In some embodiments of the compounds of Formula I, any atom not designated as deuterium is present at its natural isotopic abundance.

Also provided is a pyrogen-free pharmaceutical composition comprising a compound of Formula I and a pharmaceutically acceptable carrier. In some embodiments, the composition further comprises a second therapeutic agent useful in treating a patient suffering from or susceptible to a disease or condition selected from emotional lability; pseudobulbar affect; autism; neurological disorders; neurodegenerative diseases; brain injury; disturbances of consciousness disorders; cardiovascular diseases; glaucoma; tardive dyskinesia; diabetic neuropathy; retinopathic diseases; diseases or disorders caused by homocysteine-induced apoptosis; diseases or disorders caused by elevated levels of homocysteine; pain, including but not limited to, chronic pain; intractable pain; neuropathic pain; sympathetically mediated pain; and pain associated with gastrointestinal dysfunction; epileptic seizures; tinnitus; sexual dysfunction; intractable coughing; dermatitis; addiction disorders; Rett syndrome (RTT); voice disorders due to uncontrolled laryngeal muscle spasms; methotrexate neurotoxicity; fatigue caused by cancer; and conditions related to exposure to chemical agents. Such chemical agents may include toxic agents such as, for example, (i) agents used in warfare or combat, such as for example nerve gas, or (ii) industrial pollutants.

In some embodiments, the second therapeutic agent is selected from quinidine, quinidine sulfate, oxycodone, and gabapentin.

Also provided is a method of treating a subject suffering from or susceptible to a disease or condition selected from emotional lability; pseudobulbar affect; autism; neurological disorders; neurodegenerative diseases; brain injury; disturbances of consciousness disorders; cardiovascular diseases; glaucoma; tardive dyskinesia; diabetic neuropathy; retinopathic diseases; diseases or disorders caused by homocysteine-induced apoptosis; diseases or disorders caused by elevated levels of homocysteine; pain, including but not limited to, chronic pain; intractable pain; neuropathic pain; sympathetically mediated pain; and pain associated with gastrointestinal dysfunction; epileptic seizures; tinnitus; sexual dysfunction; intractable coughing; dermatitis; addiction disorders; Rett syndrome (RTT); voice disorders due to uncontrolled laryngeal muscle spasms; methotrexate neurotoxicity; fatigue caused by cancer; and conditions related to exposure to chemical agents, comprising the step of administering to the subject in need thereof a therapeutically effective amount of a pharmaceutical composition comprising a compound of Formula I. In some embodiments, the subject is suffering from or susceptible to diabetic neuropathic pain.

DETAILED DESCRIPTION

Definitions

Figure 1:
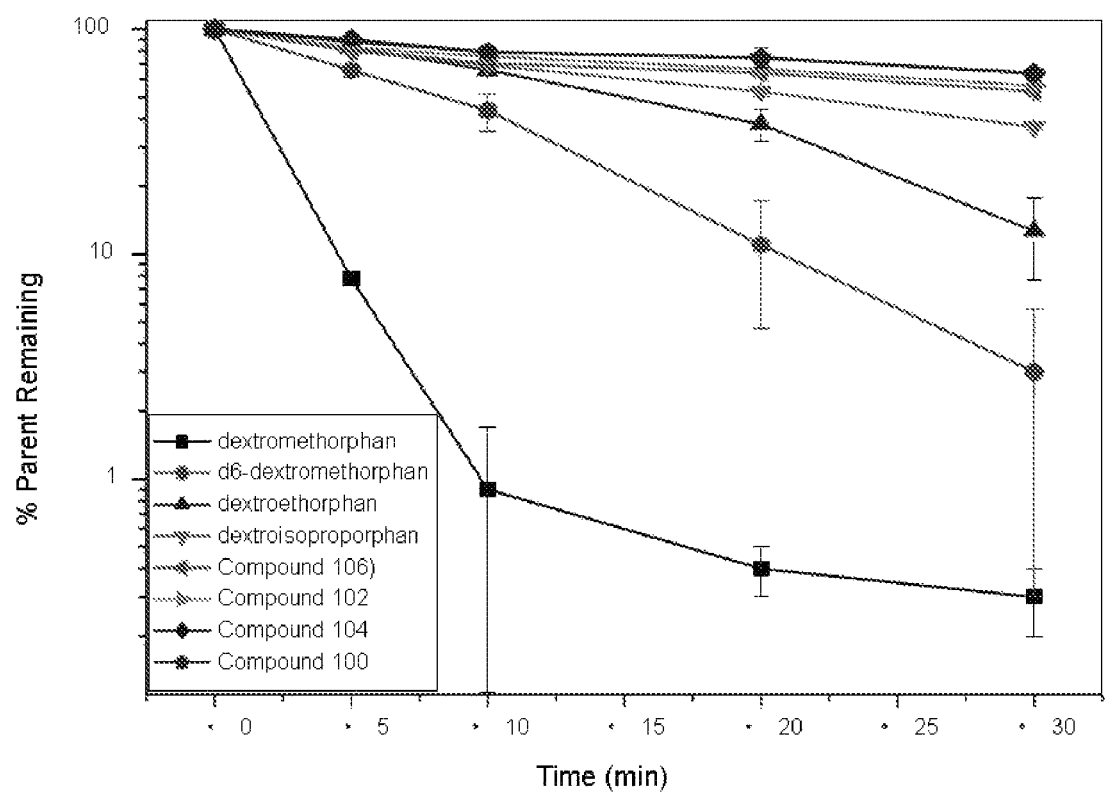
FIG. 1 depicts the metabolic stability of compounds of this invention in CYP2D6 SUPERSOMES™.

The terms "ameliorate" and "treat" are used interchangeably and include both therapeutic treatment and/or prophylactic treatment (reducing the likelihood of development). Both terms mean decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of dextromethorphan or dextromethorphan analogs will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada E et al., Seikagaku 1994, 66:15; Gannes L Z et al., Comp Biochem Physiol Mol Integr Physiol 1998, 119:725. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., the term "D" or "deuterium" indicates at least 50.1% incorporation of deuterium).

The term "isotopic enrichment factor" as used herein means the ratio between the isotopic abundance of D at a specified position in a compound of this invention and the naturally occurring abundance of that isotope. The natural abundance of deuterium is 0.015%.

In other embodiments, a compound of this invention has an isotopic enrichment factor for each deuterium present at a site designated as a potential site of deuteration on the compound of at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It is understood that the isotopic enrichment factor of each deuterium present at a site designated as a site of deuteration is independent of other deuterated sites. For example, if there are two sites of deuteration on a compound one site could be deuterated at 52.5% while the other could be deuterated at 75%. The resulting compound would be considered to be a compound wherein the isotopic enrichment factor is at least 3500 (52.5%).

The term "isotopologue" refers to a species that has the same chemical structure and formula as a specific compound of this invention, with the exception of the positions of isotopic substitution and/or level of isotopic enrichment at one or more positions, e.g., H vs. D.

The term "compound," as used herein, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues will be less than 49.9% of the compound.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any suitable salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"Stereoisomer" refers to both enantiomers and diastereomers. "D" refers to deuterium. "Tert", "$^t$", and "t" each refer to tertiary. "US" refers to the United States of America. "FDA" refers to Food and Drug Administration. "NDA" refers to New Drug Application. "rt" and "RT" refer to room temperature. "h" refers to hours. "DMF" refers to dimethylformamide. "TsOH" refers to p-toluenesulfonic acid.

Throughout this specification, a variable may be referred to generally (e.g., "each R") or may be referred to specifically (e.g., $R^1$ or $R^2$). Unless otherwise indicated, when a variable is referred to generally, it is meant to include all specific embodiments of that particular variable.

Therapeutic Compounds

The present invention provides a compound of Formula I:

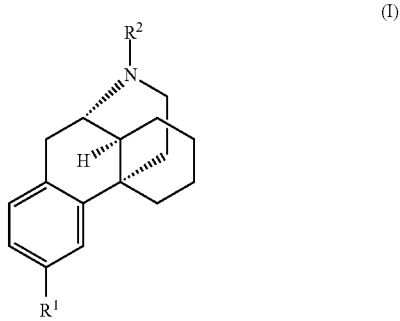

(I)

or a pharmaceutically acceptable salt thereof, wherein:
$R^1$ is —O—$(C_2$-$C_4)$alkyl or —$(C_1$-$C_4)$alkyl, wherein $R^1$ is optionally substituted with one or more deuterium atoms; and
$R^2$ is $CH_3$, $CH_2D$, $CHD_2$, or $CD_3$;
provided that at least one deuterium atom is present at either $R^1$ or $R^2$.

The preferred stereochemistry of the present compounds is based on the stereochemistry of morphinan compounds such as dextromethorphan, which exists as the dextrorotatory enantiomer of levorphanol.

One embodiment of the invention provides a compound of Formula I wherein $R^1$ is —O—($C_2$-$C_4$)alkyl which is optionally substituted with one or more deuterium atoms. In one aspect of this embodiment, $R^1$ is —O—$CH_2CH_3$, —O—$CD_2CD_3$, —O—$CD_2CH_3$, —O—$CH_2CD_3$, —O—$CH(CH_3)_2$, —O—$CD(CD_3)_2$, —O—$CH(CD_3)_2$, —O—$CD(CH_3)_2$, —O—$CH_2CH(CH_3)_2$, —O—$CD_2CH(CH_3)_2$, —O—$CH_2CD(CH_3)_2$, —O—$CH_2CH(CD_3)_2$, —O—$CD_2CD(CH_3)_2$, —O—$CD_2CH(CD_3)_2$, —O—$CH_2CD(CD_3)_2$, or —O—$CD_2CD(CD_3)_2$.

In another aspect, $R^1$ is —O—$CD_2CD_3$, —O—$CD_2CH_3$, —O—$CH_2CD_3$, —O—$CD(CD_3)_2$, —O—$CH(CD_3)_2$, —O—$CD(CH_3)_2$, —O—$CD_2CH(CH_3)_2$, —O—$CH_2CD(CH_3)_2$, —O—$CD_2CD(CH_3)_2$, —O—$CD_2CH(CD_3)_2$, —O—$CH_2CD(CD_3)_2$, or —O—$CD_2CD(CD_3)_2$.

In another aspect, $R^1$ is —O—$CD_2CD_3$, —O—$CD_2CH_3$, —O—$CH_2CD_3$, —O—$CD(CD_3)_2$, —O—$CH(CD_3)_2$, or —O—$CD(CH_3)_2$.

In another aspect, $R^1$ is —O—$CD_2CD_3$ or —O—$CD(CD_3)_2$. In another aspect, $R^1$ is —O—$CD_2CD_3$.

In another aspect, $R^1$ is —O—$CD(CD_3)_2$.

Another embodiment of Formula I provides a compound of Formula I wherein $R^1$ is a deuterated —O—($C_2$-$C_4$)alkyl and $R^2$ is —$CD_3$ or —$CH_3$. In one aspect of this embodiment, $R^2$ is —$CD_3$. In another aspect $R^2$ is —$CH_3$.

Each of the above aspects of $R^1$ may be combined with each of the above aspects of $R^2$ to form further embodiments of this invention.

Examples of specific compounds where $R^1$ is —O—($C_2$-$C_4$)alkyl include those shown in Table 1:

TABLE 1

Exemplary Compounds of Formula I ($R^1$ is —O—($C_2$—$C_4$)alkyl)

| Compound No. | $R^1$ | $R^2$ |
|---|---|---|
| 100 | —O—$CD_2CD_3$ | $CD_3$ |
| 101 | —O—$CD_2CH_3$ | $CD_3$ |
| 102 | —O—$CD(CD_3)_2$ | $CD_3$ |
| 103 | —O—$CD(CH_3)_2$ | $CD_3$ |
| 104 | —O—$CD_2CD_3$ | $CH_3$ |
| 105 | —O—$CD_2CH_3$ | $CH_3$ |
| 106 | —O—$CD(CD_3)_2$ | $CH_3$ |
| 107 | —O—$CD(CH_3)_2$ | $CH_3$ | or a pharmaceutically acceptable salt thereof.

Another embodiment of this invention provides compounds of Formula I wherein $R^1$ is —($C_1$-$C_4$)alkyl which is optionally substituted with one or more deuterium atoms. In one aspect of this embodiment, $R^1$ is —$CH_3$, —$CD_3$, —$CH_2CH_3$, —$CD_2CD_3$, —$CD_2CH_3$, —$CH_2CD_3$, —$CH_2CH_2CH_3$, —$CD_2CH_2CH_3$, —$CD_2CD_2CH_3$, —$CD_2CD_2CD_3$, —$CH_2CD_2CH_3$, —$CH_2CD_2CD_3$, —$CH_2CH_2CD_3$, —$CH(CH_3)_2$, —$CD(CD_3)_2$, —$CH(CD_3)_2$, —$CD(CH_3)_2$, —$CH_2CH_2CH_2CH_3$, —$CD_2CH_2CH_2CH_3$, —$CD_2CD_2CH_2CH_3$, —$CD_2CD_2CD_2CH_3$, —$CD_2CD_2CD_2CD_3$, —$CD_2CH_2CH_2CD_3$, —$CD_2CH_2CD_2CD_3$, —$CH_2CD_2CH_2CH_3$, —$CH_2CH_2CD_2CH_3$, —$CH_2CH_2CH_2CD_3$, —$CH_2CD_2CD_2CD_3$, —$CH_2CH_2CD_2CD_3$, —$CH(CH_3)CH_2CH_3$, —$CH(CH_3)CH_2CH_3$, —$CD(CH_3)CH_2CH_3$, —$CD(CD_3)CD_2CH_3$, —$CD(CD_3)CD_2CH_3$, —$CD(CH_3)CH_2CH_3$, —$CD(CH_3)CD_2CH_3$, —$CD(CH_3)CH_2CD_3$, —$CH(CD_3)CH_2CH_3$, —$CH(CH_3)CD_2CH_3$, —$CH(CH_3)CH_2CD_3$, —$CH(CD_3)CD_2CH_3$, $CH(CD_3)CH_2CD_3$, —$CH(CH_3)CD_2CD_3$, —$CH(CH_3)_2$, —$CD_2CH(CH_3)_2$, —$CH_2CD(CH_3)_2$, —$CH_2CH(CD_3)_2$, —$CD_2CD(CH_3)_2$, —$CD_2CH(CD_3)_2$, —$CH_2CD(CD_3)_2$, or —$CD_2CD(CD_3)_2$.

In another aspect, $R^1$ is —$CH_3$, —$CH_2CH_3$, —$CH(CH_3)_2$, or —$CH_2CH(CH_3)_2$ and $R^2$ is selected from $CD_3$. In another aspect, $R^1$ is —$CD_3$, —$CD_2CD_3$, —$CD_2CH_3$, —$CH_2CD_3$, —$CD(CD_3)_2$, —$CH(CD_3)_2$, —$CD(CH_3)_2$, —$CD_2CH(CH_3)_2$, —$CH_2CD(CH_3)_2$, —$CH_2CH(CD_3)_2$, —$CD_2CD$, $(CH_3)_2$, —$CD_2CH(CD_3)_2$, —$CH_2CD(CD_3)_2$, or —$CD_2CD$ $(CD_3)_2$. In another aspect, $R^1$ is —$CD_3$, —$CD_2CD_3$, or —$CD_2CD(CD_3)_2$. In another aspect, $R^1$ is —$CD_3$. Each of these aspects of $R^1$ may be combined with the below aspects of $R^2$ to provide further embodiments of this invention.

Another embodiment of this invention provides compounds of Formula I wherein $R^1$ is a deuterated —($C_1$-$C_4$) alkyl and wherein $R^2$ is —$CH_3$ or —$CD_3$. In one aspect of this embodiment, $R^2$ is —$CH_3$. In another aspect, $R^2$ is —$CD_3$.

Examples of specific compounds of Formula I where $R^1$ is —($C_1$-$C_4$)alkyl include Compounds 108, 109 and 110 shown below:

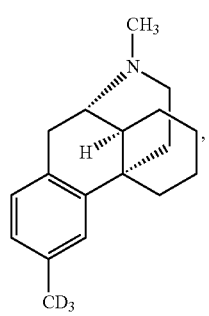

Compound 108

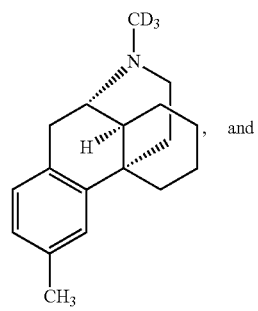

Compound 109

, and

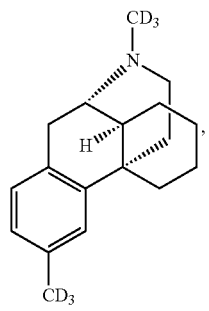

Compound 110

, or a pharmaceutically acceptable salt thereof.

In another set of embodiments, any atom not designated as deuterium in any of the embodiments set forth above is present at its natural isotopic abundance.

In another set of embodiments, the compound of Formula I is purified, e.g., the compound of Formula I is present at a purity of at least 50.1% by weight (e.g., at least 52.5%, 55%, 60%, 65%, 70%, 75%, 80%, 85%, 90%, 95%, 97%, 98%, 98.5%, 99%, 99.5% or 99.9%) of the total amount of isotopologues of Formula I present, respectively. Thus, in some embodiments, a composition comprising a compound of Formula I can include a distribution of isotopologues of the compound, provided at least 50.1% of the isotopologues by weight are the recited compound.

In another set of embodiments, the compounds of Formula I are provided in isolated form, e.g., the compound is not in a cell or organism and the compound is separated from some or all of the components that typically accompany it in nature.

In some embodiments, any position in the compound of Formula I designated as having D has a minimum deuterium incorporation of at least 50.1% (e.g., at least 52.5%, at least 60%, at least 67.5%, at least 75%, at least 82.5%, at least 90%, at least 95%, at least 97%, at least 99%, or at least 99.5%) at the designated position(s) of the compound of Formula I. Thus, in some embodiments, a composition comprising a compound of Formula I can include a distribution of isotopologues of the compound, provided at least 50.1% of the isotopologues include a D at the designated position(s).

In some embodiments, a compound of Formula I is "substantially free of" other isotopologues of the compound, e.g., less than 49.9%, less than 25%, less than 10%, less than 5%, less than 2%, less than 1%, or less than 0.5% of other isotopologues are present.

The synthesis of compounds of Formula I can be readily achieved by reference to the Exemplary Syntheses and Examples disclosed herein, and by use of procedures and intermediates analogous to those disclosed, for instance, in Schnider, O. & Grussner, A., Helv. Chim. Acta., 1951, 34: 2211; Grussner, A. & Schnider, O.; GB 713146 (1954); Toyo Pharma K. K., Japan JP 60089474 A (1983); Newman, A. H. et al., J. Med. Chem., 1992, 35: 4135. Such methods can be carried out by utilizing corresponding deuterated and, optionally, other isotope-containing reagents and/or intermediates to synthesize the compounds delineated herein, or by invoking standard synthetic protocols known in the art for introducing isotopic atoms to a chemical structure.

Exemplary Syntheses

The following deuterated reagents and building blocks which may be of use in preparing compounds of Formula I are commercially available: iodoethane-$d_5$, ethyl-2,2,2-$d_3$ iodide, ethyl-1,1-$d_2$ iodide, isopropyl-$d_7$ iodide, isopropyl-$d_7$ bromide, isopropyl-1,1,1,3,3,3-$d_6$ iodide, and 1,1,1,3,3,3-$d_6$ bromide.

A convenient method for synthesizing compounds of Formula I wherein $R^1$ is —O—($C_2$-$C_4$)alkyl is depicted in Scheme 1.

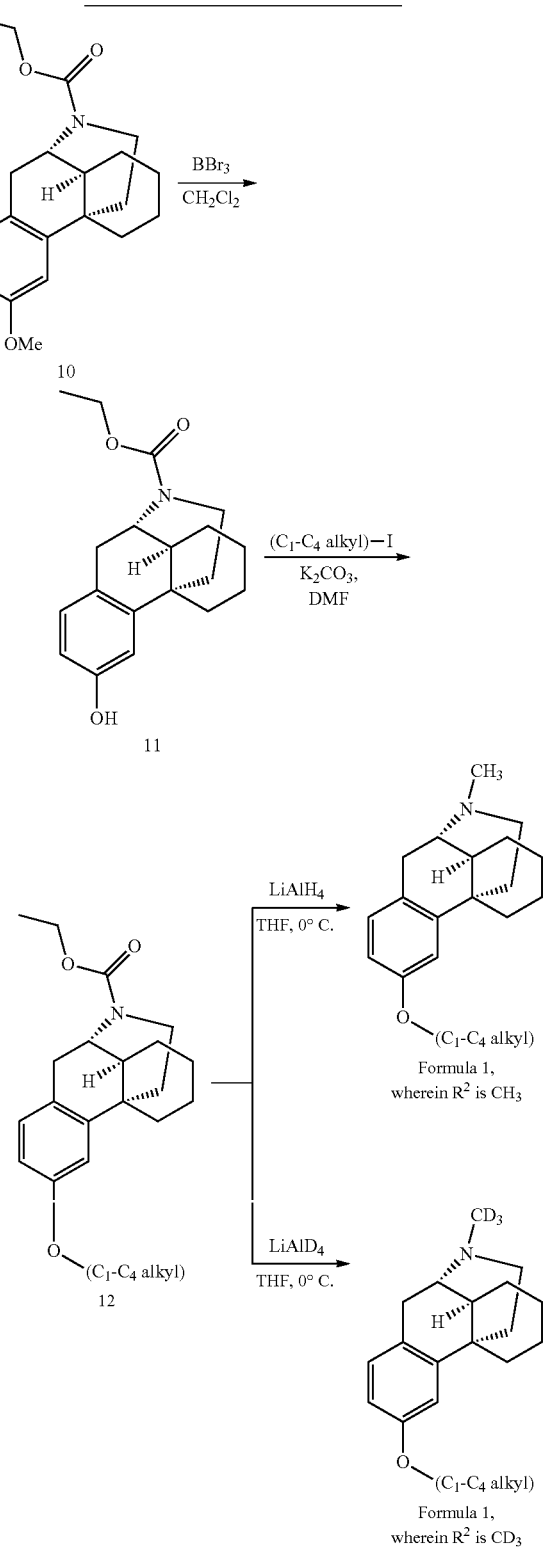

Treatment of the known 17-ethoxycarbonyl-3-methoxy-morphinan (10) (for its preparation, see: Murdter, T. E. et al., Journal of Labelled Compounds and Radiopharmaceuticals 2002, 45: 1153-1158) with boron tribromide according to the procedure described by Newman, A. H. et al., Journal of Medicinal Chemistry 1992, 35: 4135-4142, affords the 17-ethoxycarbonyl-3-hydroxy-morphinan (11). Treatment of the 3-hydroxy-morphinan 11 with the appropriately deuterated alkyl iodide in the presence of potassium carbonate in a manner analogous to the procedure described in the aforementioned paper gives the deuterated 17-ethoxycarbonyl-3-alkoxy-morphinans (12). Reduction of the carbamate of the morphinan 12 with either lithium aluminum hydride or lithium aluminum deuteride in THF in a manner analogous to that described by Newman affords the deuterated 3-alkoxy-17-methyl-morphinan (13) or the 3-alkoxy-17-trideuteromethyl-morphinan (14) compounds of Formula I, respectively.

A convenient method for synthesizing compounds of Formula I wherein $R^1$ is —$(C_1$-$C_4)$alkyl is depicted in Scheme 2.

Treatment of 17-ethoxycarbonyl-3-hydroxy-morphinan (11) with N-Phenyl-trifluoromethanesulfonimide according to the procedure described by Kim, C.-H. in US 2005/0256147 A1 affords the corresponding phenolic triflate (15). Palladium catalyzed cross-coupling of 15 with the appropriately deuterated $(C_1$-$C_4)$alkyl boronic acid (16) in a manner analogous to the procedure from the aforementioned patent gives the deuterated 17-ethoxycarbonyl-3-$(C_1$-$C_4)$ alkyl-morphinans (17). Reduction of the carbamate of morphinan 17 with either lithium aluminum hydride or lithium aluminum deuteride in THF in a manner analogous to the procedure described by Newman, A. H. et al., Journal of Medicinal Chemistry 1992, 35: 4135-4142 affords the deuterated 3-$(C_1$-$C_4)$alkyl-17-methyl-morphinan or the 3-$(C_1$-$C_4)$alkyl-17-trideuteromethyl-morphinan compounds of Formula I, respectively.

The alkylboronic acid reagent 16 used in Scheme 2 is prepared as described above in Scheme 3.

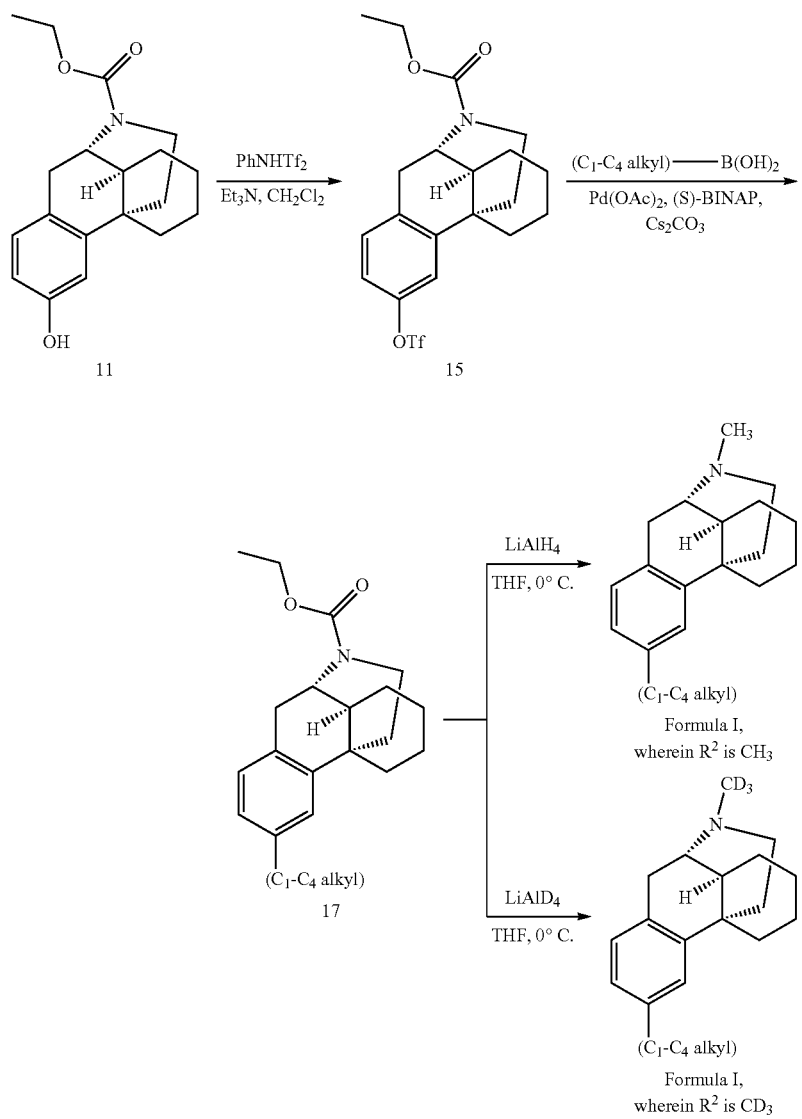

Scheme 2. Synthesis of a Compound of Formula I ($R^1$ is —$(C_1$-$C_4)$alkyl)

Scheme 3. Synthesis of Alkylboronic Ester 16

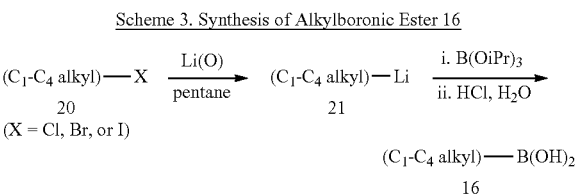

Treatment of appropriately deuterated ($C_1$-$C_4$)alkyl halide (20) with elemental lithium in pentane in a manner analogous to the procedure described by Dawildowski, D. et al., in WO 2005/082911 A1 affords the corresponding ($C_1$-$C_4$) alkyl lithium anion, which may be immediately treated with triisopropyl borate followed by hydrolysis with aqueous hydrogen chloride in a manner analogous to the procedure described by Brown, H. C. et al., Organometallics 1985, 4: 816-821 to afford the appropriately deuterated ($C_1$-$C_4$)alkyl boronic acids (16).

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$ or $R^2$) or not. The suitability of a chemical group in a compound structure for use in the synthesis of another compound is within the knowledge of one of ordinary skill in the art. Additional methods of synthesizing compounds of Formula I and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, Comprehensive Organic Transformations, VCH Publishers (1989); Greene T W et al., Protective Groups in Organic Synthesis, 3$^{rd}$ Ed., John Wiley and Sons (1999); Fieser L et al., Fieser and Fieser's Reagents for Organic Synthesis, John Wiley and Sons (1994); and Paquette L, ed., Encyclopedia of Reagents for Organic Synthesis, John Wiley and Sons (1995) and subsequent editions thereof.

Combinations of substituents and variables envisioned by this invention are only those that result in the formation of stable compounds.

Compositions

The invention also provides pyrogen-free compositions comprising a compound of Formula I (e.g., including any of the formulae herein), or a pharmaceutically acceptable salt of said compound; and an acceptable carrier. In one embodiment, the composition comprises an effective amount of the compound or pharmaceutically acceptable salt thereof. Preferably, a composition of this invention is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the subject, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as dextromethorphan. Such agents include those indicated as being useful in combination with dextromethorphan, including but not limited to, those described in U.S. Pat. Nos. 4,316,888; 4,446,140; 4,694,010; 4,898,860; 5,166,207; 5,336,980; 5,350,756; 5,366,980; 5,863,927; RE38,115; 6,197,830; 6,207,164; 6,583,152; and 7,114,547; as well as in US patent publications 2001/0044446; 2002/0103109; 2004/0087479; 2005/0129783; 2005/0203125; and 2007/0191411.

Preferably, the second therapeutic agent is an agent useful in the treatment or prevention of a disease or condition selected from emotional lability; pseudobulbar affect; autism; neurological disorders and neurodegenerative diseases, such as, e.g., dementia, amyotrophic lateral sclerosis (ALS, also known as Leu Gehrig's disease), Alzheimer's disease, Parkinson's disease, and multiple sclerosis; brain injuries, such as, e.g., stroke, traumatic brain injury, ischemic event, hypoxic event and neuronal death; disturbances of consciousness disorders; cardiovascular diseases, such as, e.g., peripheral vascular diseases, myocardial infarctions, and atherosclerosis; glaucoma, tardive dyskinesia; diabetic neuropathy; retinopathic diseases; diseases or disorders caused by homocysteine-induced apoptosis; diseases or disorders caused by elevated levels of homocysteine; chronic pain; intractable pain; neuropathic pain, sympathetically mediated pain, such as, allodynia, hyperpathia, hyperalgesia, dysesthesia, paresthesia, deafferentation pain, and anesthesia dolorosa pain; pain associated with gastrointestinal dysfunction, including, e.g., irritable bowel syndrome; mouth pain; epileptic seizures; tinnitus; sexual dysfunction; intractable coughing; dermatitis; addiction disorders, such as, e.g., addiction to or dependence on stimulants, nicotine, morphine, heroine, other opiates, amphetamines, cocaine, and alcohol; Rett syndrome (RTT); voice disorders due to uncontrolled laryngeal muscle spasms, including e.g., abductor spasmodic dysphonia, adductor spasmodic dysphonia, muscular tension dysphonia, and vocal tremor; methotrexate neurotoxicity; and fatigue caused by cancer.

In one embodiment, the second therapeutic agent is selected from quinidine, quinidine sulfate, LBH589 (Novartis), oxycodone, and gabapentin.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In one embodiment of the pharmaceutical compositions of the invention, the compound of the present invention is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the subject. See, e.g., Scientific Tables, Geigy Pharmaceuticals, Ardsley, N.Y., 1970, 537.

In one embodiment, an effective amount of a compound of this invention can range from 0.4 mg to 400 mg, from 4.0 mg to 350 mg, from 10 mg to 90 mg, or from 30 mg to 45 mg, inclusive, which can be given once, twice, or up to three times daily depending on various factors recognized by those skilled in the art.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician. For example, guidance for selecting an effective dose can be determined by reference to the prescribing information for dextromethorphan.

For pharmaceutical compositions that comprise a second therapeutic agent, an effective amount of the second therapeutic agent is between about 0.01% to 100% of the dosage normally utilized in a monotherapy regime using just that agent. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of modulating the activity of the sigma-1 and sigma-2 receptor, N-methyl-D-aspartate (NMDA), or the activity of the α3β4 nicotinic receptor in a cell, comprising contacting a cell with one or more compounds of Formula I.

In another embodiment, the invention provides a method of inhibiting neurotransmitters, such as glutamate, from activating receptors in the brain and/or inhibiting the uptake of dopamine and serotonin by administering a compound of Formula I.

According to another embodiment, the invention provides a method of treating a subject suffering from, or susceptible to, a disease or condition that is beneficially treated by dextromethorphan comprising the step of administering to said subject an effective amount of a compound of Formula I or a pharmaceutically acceptable salt thereof or a composition comprising such compound. Such diseases and conditions are well known in the art and are disclosed in, but not limited to, those described in U.S. Pat. Nos. 4,316,888; 4,446,140; 4,694,010; 4,898,860; 5,166,207; 5,336,980; 5,350,756; 5,366,980; 5,863,927; RE38,115; 6,197,830; 6,207,164; 6,583,152; and 7,114,547; as well as in US patent publications 2001/0044446; 2002/0103109; 2004/0087479; 2005/0129783; 2005/0203125; and 2007/0191411.

Such diseases and conditions include, but are not limited to, emotional lability; pseudobulbar affect; autism; neurological disorders and neurodegenerative diseases, such as, e.g., dementia, amyotrophic lateral sclerosis (ALS, also known as Leu Gehrig's disease), Alzheimer's disease, and multiple sclerosis; disturbances of consciousness disorders; cardiovascular diseases, such as, e.g., peripheral vascular diseases, strokes, myocardial infarctions, and atherosclerosis; glaucoma, tardive dyskinesia; diabetic neuropathy; retinopathic diseases; diseases or disorders caused by homocysteine-induced apoptosis; diseases or disorders caused by elevated levels of homocysteine; pain, including but not limited to, chronic pain; intractable pain; neuropathic pain, sympathetically mediated pain, such as, allodynia, hyperpathia, hyperalgesia, dysesthesia, paresthesia, deafferentation pain, and anesthesia delorosa pain; pain associated with gastrointestinal dysfunction, including, e.g., irritable bowel syndrome; and mouth pain; epileptic seizures; tinnitus; sexual dysfunction; intractable coughing; dermatitis; addiction disorders, such as, e.g., addiction to or dependence on stimulants, nicotine, morphine, heroine, other opiates, amphetamines, cocaine, and alcohol; Rett syndrome (RTT); voice disorders due to uncontrolled laryngeal muscle spasms, including e.g., abductor spasmodic dysphonia, adductor spasmodic dysphonia, muscular tension dysphonia, and vocal tremor; methotrexate neurotoxicity; fatigue caused by cancer; and conditions related to exposure to chemical agents.

In one particular embodiment, the method of this invention is used to treat a subject suffering from or susceptible to a disease or condition selected from diabetic neuropathy, Rett syndrome (RTT); voice disorders due to uncontrolled laryngeal muscle spasms, including e.g., abductor spasmodic dysphonia, adductor spasmodic dysphonia, muscular tension dysphonia, and vocal tremor; methotrexate neurotoxicity; and fatigue caused by cancer.

In one particular embodiment, the method is used to treat a subject suffering from or susceptible neuropathic pain. In another embodiment, the method is used to treat a subject suffering from pseudobulbar affect.

In another particular embodiment, the method is used to treat a subject suffering from generalized epileptic seizures or partial epileptic seizures.

Methods delineated herein also include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In another embodiment, any of the above methods of treatment comprises the further step of co-administering to the subject one or more additional second therapeutic agents. The choice of second therapeutic agent may be made from any second therapeutic agent known to be useful for co-administration with dextromethorphan. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In particular, the combination therapies of this invention include co-administering to a subject in need thereof a compound of Formula I or pharmaceutically acceptable salt thereof, or a composition comprising such compound or salt; and quinidine sulfate wherein the subject is suffering from or susceptible to diabetic neuropathy.

In another embodiment the invention provides a method of treating a subject suffering from non-small cell lung cancer or malignant pleural mesothelioma by co-administering to the subject in need thereof a compound of Formula I, or a composition comprising such compound; and LBH589.

The term "co-administered" as used herein means that the additional second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I alone or together with one or more of the above-described second therapeutic agents in the manufacture of a medicament, either as a single composition or as separate dosage forms, for treatment or prevention in a subject of a disease, disorder or symptom set forth above. Another aspect of the invention is a compound of Formula I for use in the treatment or prevention in a subject of a disease, disorder or symptom thereof delineated herein.

Diagnostic Methods and Kits

The compounds and compositions of this invention are also useful as reagents in methods for determining the concentration of dextromethorphan in solution or biological sample such as plasma, examining the metabolism of dextromethorphan and other analytical studies.

According to one embodiment, the invention provides a method of determining the concentration, in a solution or a biological sample, of a non-deuterated analog of a compound of Formula I, comprising the steps of:
- a) adding a known concentration of a compound of Formula I to the solution of biological sample;
- b) subjecting the solution or biological sample to a measuring device that distinguishes the corresponding non-deuterated analog from a compound of Formula I;
- c) calibrating the measuring device to correlate the detected quantity of the compound of Formula I with the known concentration of the compound of Formula I added to the biological sample or solution; and
- d) measuring the quantity of the corresponding non-deuterated analog in the biological sample with said calibrated measuring device; and
- e) determining the concentration of the corresponding non-deuterated analog in the solution of sample using the correlation between detected quantity and concentration obtained for a compound of Formula I.

Measuring devices that can distinguish the corresponding non-deuterated analog from a compound of Formula I include any measuring device that can distinguish between two compounds that differ from one another in isotopic abundance. Exemplary measuring devices include a mass spectrometer, NMR spectrometer, or IR spectrometer.

In another embodiment, a method for determining the amount of a non-deuterated analog of a compound of Formula I in a solution or a biological sample is provided, comprising:
- a) adding a known amount of a compound of Formula I to the solution or biological sample;
- b) detecting at least one signal for a compound of Formula I and at least one signal for the corresponding non-deuterated analog in a measuring device that is capable of distinguishing the two compounds;
- c) correlating the at least one signal detected for a compound of Formula I with the known amount of the compound of Formula I added to the solution or the biological sample; and
- d) determining the amount of the corresponding non-deuterated analog in the solution or biological sample using the correlation between the at least one signal detected of the compound of Formula I and the amount added to the solution or biological sample of a compound of Formula I.

In another embodiment, the invention provides a method of evaluating the metabolic stability of a compound of Formula I comprising the steps of contacting the compound of Formula I with a metabolizing enzyme source for a period of time and comparing the amount of the compound of Formula I with the metabolic products of the compound of Formula I after the period of time.

In a related embodiment, the invention provides a method of evaluating the metabolic stability of a compound of Formula I in a subject following administration of the compound of Formula I. This method comprises the steps of obtaining a serum, blood, tissue, urine or feces sample from the subject at a period of time following the administration of the compound of Formula I to the subject; and comparing the amount of the compound of Formula I with the metabolic products of the compound of Formula I in the serum, blood, tissue, urine or feces sample.

The present invention also provides kits for use to treat pseudobulbar disorder, diabetic neuropathy, Rett syndrome (RTT); voice disorders due to uncontrolled laryngeal muscle spasms, including e.g., abductor spasmodic dysphonia, adductor spasmodic dysphonia, muscular tension dysphonia, and vocal tremor; methotrexate neurotoxicity; and fatigue caused by cancer. These kits comprise (a) a pharmaceutical composition comprising a compound of Formula I or a salt thereof, wherein said pharmaceutical composition is in a container; and (b) instructions describing a method of using the pharmaceutical composition to treat pseudobulbar affect; diabetic neuropathy; Rett syndrome (RTT); voice disorders due to uncontrolled laryngeal muscle spasms, including e.g., abductor spasmodic dysphonia, adductor spasmodic dysphona, muscular tension dysphonia, and vocal tremor; methotrexate neurotoxicity; and fatigue caused by cancer.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In on embodiment, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In an embodiment of the kits of this invention, the composition comprising the second active agent may be in a vessel or container that is separate from the vessel containing the composition comprising a compound of Formula I.

EXAMPLES

Example 1. Synthesis of (+)-3-(Ethoxy-d$_5$)-17-(methyl-d$_3$)-(9α,13α,14α)-morphinan hydrochloride (100)

Compound 100 was prepared as outlined below. Details of the synthesis follow.

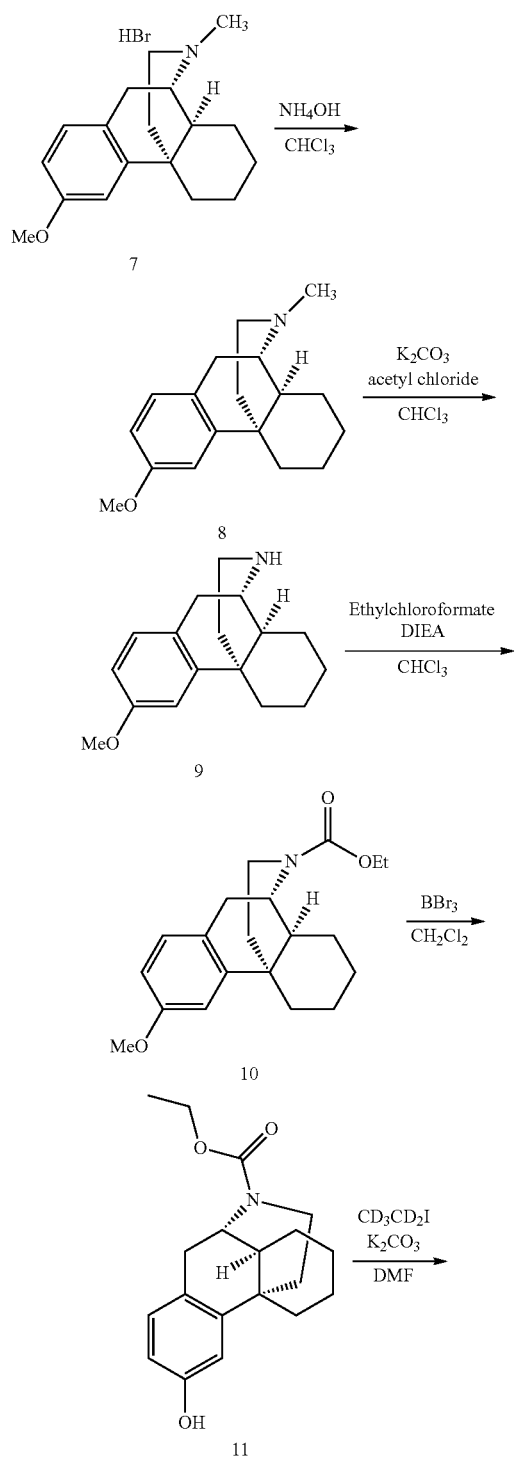

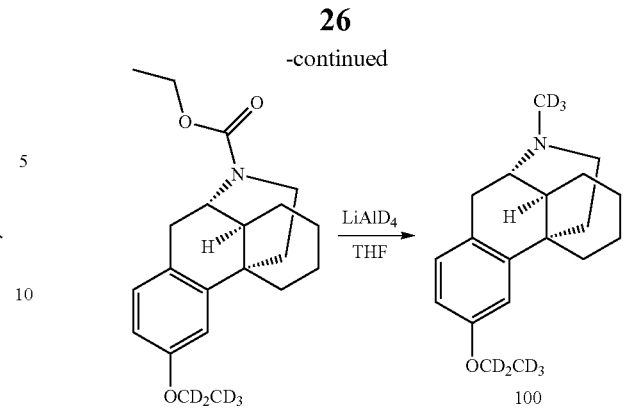

Synthesis of (+)-3-methoxy-17-methyl-(9α,13α,14α)-morphinan (free base, 8)

To a reaction vessel was added (+)-3-methoxy-17-methyl-(9α,13α,14α)-morphinan, HBr salt (7; 3.00 g, 8.5 mmol), NH$_3$ in CH$_3$OH (2.0 M, 8.5 mL, 17.0 mmol), and a stir bar. The reaction mixture was stirred at RT for 1 h. The resulting material was concentrated on a rotary evaporator, then diluted with CHCl$_3$ (50 mL) and H$_2$O (50 mL). The layers were separated and the water layer was extracted with CHCl$_3$ (50 mL). The combined organic layers were dried over magnesium sulfate, filtered and concentrated on a rotary evaporator to yield 2.88 g of 8 as a fluffy white solid.

$^1$H-NMR (300 MHz, CDCl$_3$): δ 1.12 (ddd, J$_1$=24.7, J$_2$=12.6, J$_3$=3.8, 1H), 1.23-1.43 (m, 5H), 1.49-1.52 (m, 1H), 1.62-1.65 (m, 1H), 1.72 (td, J$_1$=12.6, J$_2$=4.9, 1H), 1.81 (dt, J$_1$=12.6, J$_2$=3.3, 1H), 2.07 (td, J$_1$=12.6, J$_2$=3.3, 1H), 2.33-2.47 (m, 5H), 2.57 (dd, J$_1$=18.1, J$_2$=5.5, 1H), 2.79 (dd, J$_1$=5.5, J$_2$=3.3, 1H), 2.98 (d, J=18.1, 1H), 6.68 (dd, J$_1$=8.2, J$_2$=2.7, 1H), 6.80 (d, J=2.7, 1H), 7.02 (d, J=8.8, 1H).

Synthesis of (+)-3-methoxy-(9α,13α,14α)-morphinan (9)

The solid (+)-3-methoxy-17-methyl-(9α,13α,14α)-morphinan (8; 6.79 g, 25.1 mmol) was placed in a reaction vessel with CHCl$_3$ and a stir bar. K$_2$CO$_3$ (13.85 g, 100.2 mmol) was added and the mixture was stirred at RT under an atmosphere of N$_2$ for 10 min before the addition of acetyl chloride (7.866 g, 100.2 mmol). The resulting reaction mixture, still under an atmosphere of N$_2$, was stirred under reflux conditions for 7 h, then filtered through a pad of celite. The organic filtrate was concentrated on a rotary evaporator and the resulting crude material was dissolved in CH$_3$OH then stirred under reflux conditions for 1 h. The solution was concentrated on a rotary evaporator then dried under vacuum to yield 6.78 g of 9 as an off-white solid.

$^1$H-NMR (300 MHz, CDCl$_3$): δ 1.04-1.13 (m, 1H), 1.19-1.29 (m, 1H), 1.37-1.66 (m, 6H), 2.37 (d, J=13.5, 2H), 2.54 (bs, 1H), 2.80 (s, 2H), 2.95-2.99 (m, 1H), 3.12-3.18 (m, 2H), 3.48 (s, 1H), 3.71 (s, 3H), 6.76 (dd, J$_1$=8.3, J$_2$=2.6, 1H), 6.80 (d, J=2.3, 1H), 7.07 (d, J=8.3, 1H).

Synthesis of (+)-17-ethylcarbamate-3-methoxy-(9α,13α,14α)-morphinan (10)

To a reaction vessel fit with a stirbar was added 9 (6.025 g, 2.48 mmol) dissolved in CHCl$_3$ (100 mL). Diisopropylethylamine (DIEA; 16.32 g, 126.3 mmol) was added and the mixture was stirred for 10 min at room temperature under nitrogen before the addition of ethylchloroformate (13.094 g, 76.8 mmol). The reaction mixture was stirred under reflux conditions under nitrogen for 3 h, at which point TLC (20% ethylacetate/hexane) showed complete consumption of the starting material. The organic layer was removed and washed first with 1M HCl, and then with saturated $NaHCO_3$. The aqueous layers from each wash were combined and back extracted with 50 ml of $CHCl_3$. The organic layer from the back extraction was combined with the organic layer from the washes and the combined organic layers were dried over $Na_2SO_4$. The organic solution was then filtered, concentrated on a rotary evaporator then was purified via automated flash column chromatography (0-30% ethylacetate/hexane) to yield 5.37 g of 10 as a clear light yellow oil.

$^1$H-NMR (300 MHz, $CDCl_3$): δ 1.06 (ddd, $J_1$=25.3, $J_2$=12.6, $J_3$=3.8, 1H), 1.21-1.39 (m, 7H), 1.45-1.60 (m, 3H), 1.65-1.70 (m, 2H), 2.34-2.37 (m, 1H), 2.54-2.69 (m, 2H), 3.04-3.12 (m, 1H), 3.78 (s, 3H), 3.86 (ddd, $J_1$=42.3, $J_2$=13.7, $J_3$=3.8, 1H), 4.12 (q, J=7.14, 2H), 4.31 (dt, $J_1$=56.6, $J_2$=4.3, 1H), 6.71 (dd, $J_1$=8.8, $J_2$=2.2, 1H), 6.82 (d, J=2.7, 1H), 7.00 (apparent t, J=8.2, 1H).

Synthesis of (+)-17-ethylcarbamate-3-hydroxy-(9α,13α,14α)-morphinan (11)

In a reaction vessel fit with a stirbar the carbamate 10 (2.43 g, 7.4 mmol) was dissolved in $CH_2Cl_2$ (20 mL) and the resulting solution was cooled to 0° C. $BBr_3$ (9.24 g, 36.9 mmol) was added and the reaction mixture was stirred under an atmosphere of $N_2$ at 0° C. for 20 min (at which time tlc in 20% ethylacetate/hexane showed the reaction to be complete). A solution of 27% $NH_4OH$ in ice was placed in a beaker with a stir bar and the reaction mixture was slowly added with stirring. The resulting mixture was stirred for 20 min then was extracted with 4:1 $CHCl_3/CH_3OH$ (200 mL). The organic layer was dried over $Na_2SO_4$, filtered, then concentrated on a rotary evaporator. The crude material was purified via automated flash column chromatography ($CH_3OH$ with 1% $NH_4OH/CHCl_3$, 0-10%). The pure fractions were concentrated on a rotary evaporator to yield 1.48 g of 11 as a white solid.

$^1$H-NMR (300 MHz, $CDCl_3$): δ 1.04-1.12 (m, 1H), 1.22-1.36 (m, 7H), 1.45-1.59 (m, 3H), 1.63-1.67 (m, 2H), 2.30-2.33 (m, 1H), 2.52-2.66 (m, 2H), 3.06 (dt, $J_1$=18.4, $J_2$=5.9, 1H), 3.84 (ddd, $J_1$=35.8, $J_2$=13.8, $J_3$=6.1, 1H), 4.10-4.18 (m, 2H), 4.31 (dt, $J_1$=53.9, $J_2$=3.1, 1H), 6.64 (m, 1H), 6.78 (s, 1H), 6.93 (apparent t, J=7.8, 1H).

Synthesis of (+)-3-(ethoxy-$d_5$)-17-ethoxycarbonyl-(9α,13α,14α)-morphinan (20)

To a solution of alcohol 11 (1.50 g, 4.8 mmol) in DMF (25 mL), was added $K_2CO_3$ (2.00 g, 14.5 mmol, 3.05 eq) and iodoethane-$d_5$ (1.15 g, 7.1 mmol, 1.50 eq) with stirring. The reaction mixture was stirred overnight at room temperature (rt) under an atmosphere of $N_2$, was quenched by the addition of $H_2O$, and extracted with $Et_2O$ (3×30 mL). The combined organics were dried over $Na_2SO_4$, filtered and concentrated in vacuo to a yellow oil. Purification via automated flash column chromatography (0-40% EtOAc/hexanes) afforded intermediate 20 (1.53 g, 91% yield).

Synthesis of (+)-3-(ethoxy-$d_5$)-17-(methyl-$d_3$)-(9α,13α,14α)-morphinan hydrochloride (100)

To a slurry of $LiAlD_4$ (0.184 g, 4.4 mmol, 2.0 eq) in THF (10 mL) stirring at −78° C. was added a solution of the carbamate 20 (0.763 g, 2.2 mmol) in THF (5 mL). After 1 h of stirring at rt, no reaction was detected by tlc and an additional 2.0 eq of $LiAlD_4$ (0.184 g, 4.4 mmol, 2.0 eq) was added. The reaction mixture was stirred overnight at rt, then was quenched by the addition of magnesium sulfate heptahydrate until cessation of gas evolution. The mixture was filtered, concentrated in vacuo and the resultant crude material was purified via automated flash column chromatography ($CHCl_3/CH_3OH/NH_3OH$-90/10/1) to yield the free amine 100. This material was dissolved in 1.25 M HCl in $CH_3OH$ then was concentrated under reduced pressure and dried under high vacuum to yield 14.3 mg of product 100 as the HCl salt.

$^1$H-NMR (300 MHz, DMSO-$d_6$): δ 0.94-1.63 (m, 8H), 1.72-1.80 (m, 1H), 1.94 (d, J=11.9, 1H), 2.43-2.47 (m, 1H), 2.96 (dd, J=19.2, $J_2$=6.1, 2H), 3.09-3.17 (m, 2H), 3.57-3.61 (m, 1H), 6.79-6.82 (m, 2H), 7.11 (d, J=8.8, 1H), 9.58 (br s, 1H). HPLC (method: 150 mm C18-RP column—gradient method 5-95% ACN; Wavelength: 280 nm): retention time: 3.08 min, purity: 95%. MS (M+H): 294.2.

Example 2. Synthesis of (+)-3-(Ethoxy-$d_5$)-17-methyl-(9α,13α,14α)-morphinan hydrochloride (104)

Compound 104 was prepared as outlined in Example 1 above with the exception that $LiAlH_4$ was used in place of $LiAlD_4$ for the reduction of the carbamate 20 to 104.

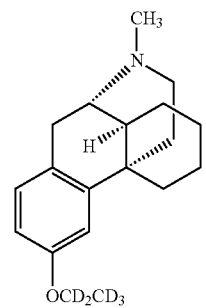

104

Synthesis of (+)-3-(ethoxy-$d_5$)-17-methyl-(9α,13α,14α)-morphinan hydrochloride (104)

To a slurry of $LiAlH_4$ (0.166 g, 4.4 mmol, 2.0 eq) in THF (10 mL) stirring at −78° C. was added a solution of the carbamate 20 (0.763 g, 2.2 mmol) in THF (5 mL). After 1 h an additional 2.0 eq of $LiAlH_4$ (0.184 g, 4.4 mmol, 2.0 eq) was added. The reaction mixture was stirred overnight at rt, then was quenched by the addition of magnesium sulfate heptahydrate until cessation of gas evolution. The mixture was filtered, concentrated in vacuo and the resultant crude material was purified via automated flash column chromatography ($CHCl_3/CH_3OH/NH_3OH$-90/10/1) to yield the free-amine 104. This material was dissolved in 1.25 M HCl in $CH_3OH$ then was concentrated under reduced pressure and dried under high vacuum to yield 31 mg of product 104 as the HCl salt.

$^1$H-NMR (300 MHz, DMSO-$d_6$): δ 0.94-1.64 (m, 8H), 1.74-1.82 (m, 1H), 1.97 (d, J=12.4, 1H), 2.44-2.47 (m, 1H), 2.81 (s, 3H), 2.96 (dd, $J_1$=20.0, $J_2$=5.8, 2H), 3.09-3.18 (m, 2H), 3.55-3.62 (m, 1H), 6.79-6.82 (m, 2H), 7.12 (d, J=9.1, 1H), 9.68 (br s, 1H). HPLC (method: 150 mm C18-RP column—gradient method 5-95% ACN; Wavelength: 280 nm): retention time: 3.00 min, purity: 95%. MS (M+H): 291.2.

Example 3. Synthesis of (+)-3-(Isopropoxy-$d_7$)-17-(methyl-$d_3$)-(9α,13α,14α)-morphinan (102)

Compound 102 was prepared as outlined below. Details of the synthesis follow.

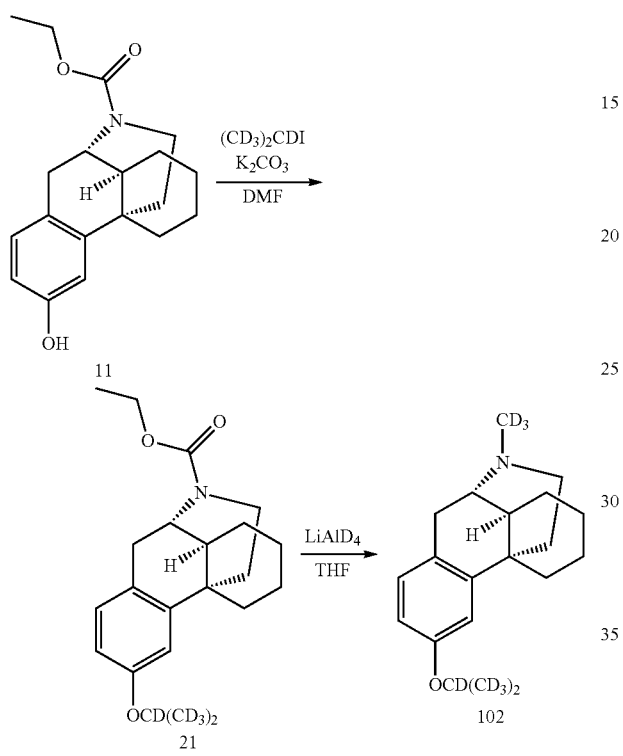

Synthesis of (+)-3-(isopropoxy-$d_7$)-17-ethoxycarbonyl-(9α,13α,14α)-morphinan (21)

To a solution of alcohol 11 (1.50 g, 4.8 mmol; produced according to Example 1) in DMF (25 mL), was added $K_2CO_3$ (2.00 g, 14.5 mmol, 3.05 eq) and 2-iodopropane-$d_7$ (0.71 mL, 7.1 mmol, 1.50 eq) with stirring. The reaction mixture was stirred overnight at room temperature (rt) under an atmosphere of $N_2$, was quenched by the addition of $H_2O$, and extracted with $Et_2O$ (3×30 mL). The combined organics were dried over $Na_2SO_4$, filtered and concentrated in vacuo to a colorless oil. Purification via automated flash column chromatography (0-40% EtOAc/hexanes) afforded intermediate 21 (1.48 g, 85% yield).

Synthesis of (+)-3-(isopropoxy-$d_7$)-17-(methyl-$d_3$)-(9α,13α,14α)-morphinan (102)

To a slurry of $LiAlD_4$ (0.340 g, 8.1 mmol, 4.0 eq) in THF (10 mL) stirring at −78° C. was added a solution of the carbamate 21 (0.739 g, 2.0 mmol) in THF (5 mL). The reaction mixture was stirred overnight at rt, then was quenched by the addition of magnesium sulfate heptahydrate until cessation of gas evolution. The mixture was filtered, the filtrate concentrated in vacuo and the resultant material was dissolved in $CH_3OH$. The resulting solution was acidified to pH 4 with fumaric acid resulting in salt precipitation. The mixture was stirred for 5 min, and $Et_2O$ was added to bring remaining salt out of solution. The salt was isolated by filtration and dried to yield 660 mg of final product 102 as the fumaric acid salt.

$^1$H-NMR (300 MHz, $CDCl_3$): δ 1.10 (qd, $J_1$=12.6, $J_2$=3.8, 1H), 1.21-1.68 (m, 7H), 2.01 (td, $J_1$=13.6, $J_2$=4.5, 1H), 2.16-2.21 (m, 1H), 2.32-2.47 (m, 2H), 2.99-3.01 (m, 2H), 3.10-3.13 (m, 1H), 3.44-3.46 (m, 1H), 6.72 (dd, $J_1$=8.4, $J_2$=2.4, 1H), 6.79 (d, J=2.5, 1H), 6.82 (s, 1H), 7.03 (d, J=8.3, 1H). HPLC (method: 150 mm C18-RP column—gradient method 5-95% ACN; Wavelength: 280 nm): retention time: 3.11 min, purity: 95%. MS (M+H): 310.3.

Example 4. Synthesis of (+)-3-(Isopropoxy-$d_7$)-17-methyl-(9α,13α,14α)-morphinan (106)

Compound 106 was prepared as outlined in Example 3 above with the exception that $LiAlH_4$ was used in place of $LiAlD_4$ for the reduction of the carbamate 21 to 106.

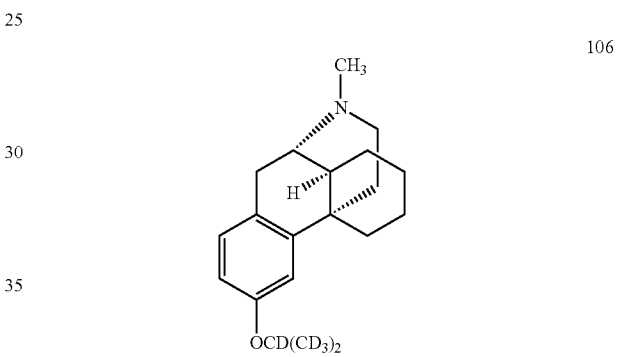

Synthesis of (+)-3-(isopropoxy-$d_7$)-17-methyl-(9α,13α,14α)-morphinan (106)

To a slurry of $LiAlH_4$ (0.308 g, 8.1 mmol, 4.0 eq) in THF (10 mL) stirring at −78° C. was added a solution of the carbamate 21 (0.739 g, 2.0 mmol) in THF (5 mL). The reaction mixture was stirred overnight at rt, then was quenched by the addition of magnesium sulfate heptahydrate until cessation of gas evolution. The mixture was filtered, the filtrate concentrated in vacuo and the resultant material was dissolved in $CH_3OH$. The resulting solution was acidified to pH 4 with fumaric acid resulting in salt precipitation. The mixture was stirred for 5 min, and $Et_2O$ was added to bring remaining salt out of solution. The salt was isolated by filtration and dried to yield 330 mg of final product 106 as the fumaric acid salt.

$^1$H-NMR (300 MHz, $CDCl_3$): δ 1.09 (qd, $J_1$=12.6, $J_2$=3.8, 1H), 1.22-1.58 (m, 6H), 1.65 (d, J=12.6, 1H), 2.06 (td, $J_1$=13.5, $J_2$=4.3, 1H), 2.20 (d, J=12.4, 1H), 2.35 (d, J=13.3, 1H), 2.46-2.53 (m, 1H), 2.78 (s, 3H), 2.96-3.12 (m, 2H), 3.25-3.30 (m, 1H), 3.62-3.64 (m, 1H), 6.73 (dd, $J_1$=8.3, $J_2$=2.5, 1H), 6.80 (d, J=2.5, 1H), 6.86 (s, 2H), 7.05 (d, J=8.3, 1H). HPLC (method: 150 mm C18-RP column—gradient method 5-95% ACN; Wavelength: 280 nm): retention time: 3.18 min, purity: 95%. MS (M+H): 307.4.

Example 5. Synthesis of (+)-3-(Methyl-d₃)-17-methyl-(9α,13α,14α)-morphinan (108)

Compound 108 was prepared as outlined below. Details of the synthesis are set forth below.

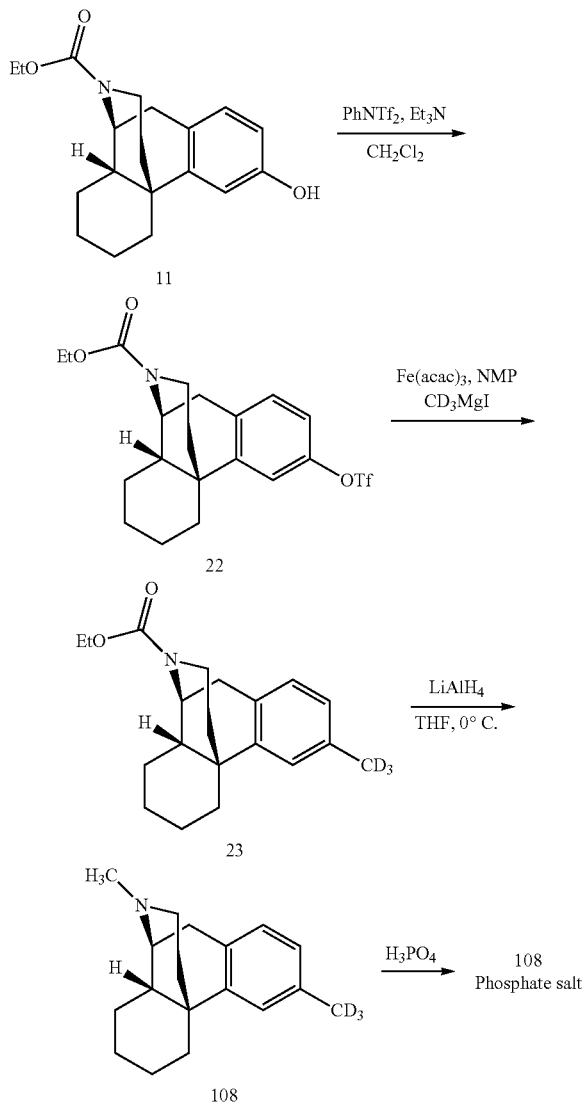

Synthesis of (+)-17-ethylcarbamate-3-trifluoromethylsulfonyloxy-(9α,13α,14α)-morphinan (22)

To a solution of 11 (9 g, 28.6 mmol, see Example 1) and triethylamine (16 mL, 114 mmol) in $CH_2Cl_2$ (400 mL) was added N-phenyl-trifluoromethanesulfonimide "$PhNTf_2$" (20.7 g, 57.2 mmol) with cooling in an ice-bath. The reaction mixture was allowed to warm to ambient temperature and was stirred overnight. The mixture was diluted with $CH_2Cl_2$ (500 mL) and the solution was washed with saturated sodium bicarbonate, water, and brine, then dried over sodium sulfate. After filtration and concentration under reduced pressure, the crude product was purified by column chromatography on silica gel (ethyl acetate/heptanes, 0-10%) to afford 12 g (94%) of 22 as clear oil.

Synthesis of (+)-17-ethylcarbamate-3-(methyl-d₃)-(9α,13α,14α)-morphinan (23)

To a solution of 22 (22 g, 43.8 mmol) in THF (500 mL) was added N-methyl-2-pyrrolidone "NMP" (26.2 mL, 153.1 mmol) at ambient temperature. The reaction mixture was degassed by $N_2$ purge for 10 minutes. Iron(III) acetylacetonate "$Fe(acac)_3$" (1.65 g, 4.4 mmol) and $CD_3MgI$ (1M in $Et_2O$, 53 mL, 47.6 mmol, Sigma Aldrich, 99 atom % D) were added and the reaction mixture was heated to reflux overnight. The reaction was cooled and water (500 mL) was added. The layers were separated and the aqueous layer was extracted with $CH_2Cl_2$ (3×100 mL). The combined organics were washed with brine, dried over sodium sulfate, filtered, concentrated under reduced pressure and purified by column chromatography on silica gel (ethyl acetate/heptanes, 0-10%) to afford 4 g (94%, based on recovered starting material) of 23 and 16 g of recovered 22.

Synthesis of (+)-3-(methyl-d₃)-17-methyl-(9α,13α,14α)-morphinan (108)

A mixture of 23 (1.5 g, 4.8 mmol) in THF (70 mL) was treated with $LiAlH_4$ (1M in THF, 19.2 mL) at 0° C. The mixture was allowed to warm to ambient temperature and was stirred overnight. Water (1 mL) was added to quench the reaction, followed by NaOH (24%, 10 mL). The mixture was stirred for 30 minutes, during which time white solid precipitated. The solid was filtered and the filtrate was concentrated under reduced pressure. The crude product was purified by preparative HPLC (see conditions described below) to afford 108. The free amine was dissolved in MTBE (30 mL) and heated to reflux. $H_3PO_4$ (in isopropanol) was added dropwise, resulting in the formation of a white solid. The addition of $H_3PO_4$ was continued until no more white solid appeared to precipitate. The solid was filtered and washed with MTBE (100 mL) to provide 1.2 g of solid. The material was recrystallized with MeOH/MTBE to provide 108 as the phosphate salt (0.75 g, 47%).

$^1$H-NMR (300 MHz, $CD_3OD$): δ 1.07-1.57 (m, 8H), 1.69-1.72 (m, 1H), 1.96-2.10 (m, 2H), 2.56 (br.d., 1H), 2.91 (s, 3H), 3.06-3.11 (br. s. and m, 3H), 3.56 (br.m., 1H), 7.03-7.18 (m, 3H). HPLC (method: 20 mm C-18 RP column—gradient method 2-95% ACN/water/0.1% formic acid; Wavelength: 210 nm): retention time: 2.59 min, purity: 99.4%. MS (M+H): 259.2

Preparative HPLC conditions:

Sunfire C18 5 um 30×150 mm column; Waters GI Pump;

Solvent A=water; Solvent B=acetonitrile

Gradient:

| Time (min) | Flow Rate (mL/min) | % A | % B |
| --- | --- | --- | --- |
| 0 | 40.00 | 90 | 10 |
| 7.00 | 40.00 | 50 | 50 |
| 8.00 | 40.00 | 5 | 95 |
| 9.00 | 20.00 | 90 | 10 |
| 10.00 | 20.00 | 90 | 10 |

Example 6. Synthesis of (+)-3-Methyl-17-(methyl-d$_3$)-(9α,13α,14α)-morphinan (109)

Compound 109 was prepared as outlined below. Details of the synthesis follow.

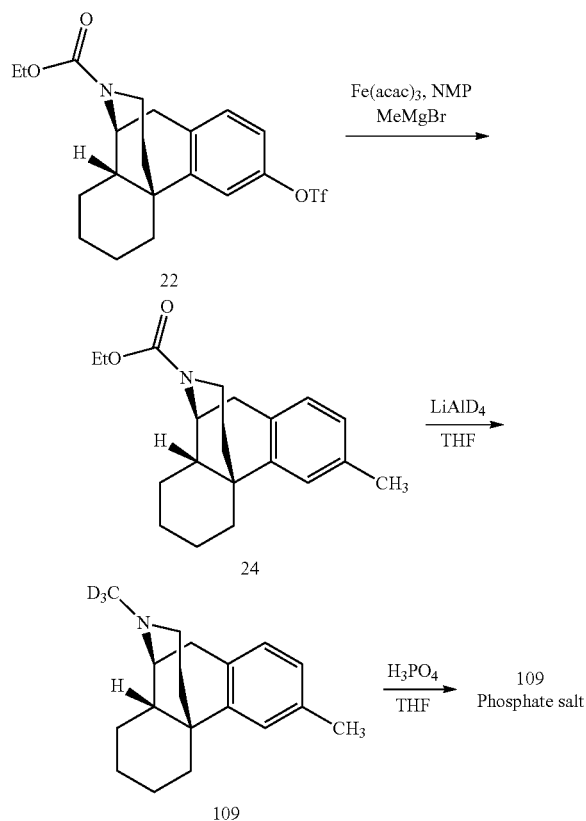

109

Synthesis of (+)-17-ethylcarbamate-3-methyl-(9α, 13α,14α)-morphinan (24)

To a solution of 22 (3.6 g, 7.16 mmol, see Example 5) in THF (100 mL) was added N-methyl-2-pyrrolidone "NMP" (4.3 mL, 25.1 mmol) at ambient temperature. The reaction mixture was degassed by N$_2$ purge for 10 minutes. Iron(III) acetylacetonate "Fe(acac)$_3$" (270 mg, 0.72 mmol) and MeMgBr (3M in Et$_2$O, 2.9 mL, 7.8 mmol) were added and the reaction mixture was heated to reflux overnight. The reaction was cooled and water (50 mL) was added. The layers were separated and the aqueous layer was extracted with CH$_2$Cl$_2$ (3×100 mL). The combined organics were washed with brine, dried over sodium sulfate, filtered, concentrated under reduced pressure, and purified by column chromatography on silica gel (ethyl acetate/heptanes, 0-10%) to give 0.84 g of 24 (75% based on recovered starting material) and 2 g of recovered 22.

Synthesis of (+)-3-methyl-17-(methyl-d$_3$)-(9α,13α, 14α)-morphinan (109)

A mixture of 24 (1 g, 6.2 mmol) in THF (30 mL) was treated with LiAlD$_4$ (0.9 g, 24.8 mmol, Cambridge Isotopes, 98 atom % D) at 0° C. and the reaction was allowed to warm to ambient temperature and stir overnight. Water (1 mL) was added to quench the reaction, followed by NaOH (24%, 5 mL). The mixture was stirred for 30 minutes, during which time white solid precipitated. The solid was filtered and the filtrate was concentrated under reduced pressure. The crude product was dissolved in EtOAc (30 mL) and extracted with 10% HCl (3×30 mL). The combined aqueous layer was washed with CH$_2$Cl$_2$ (30 mL) and neutralized with 10% NaOH. The aqueous layer was then extracted with CH$_2$Cl$_2$ (3×30 mL), the combined organics were dried over sodium sulfate, filtered and concentrated under reduced pressure to afford 109. The free amine was dissolved in MTBE (30 mL) and heated to reflux. H$_3$PO$_4$ (in isopropanol) was added dropwise, resulting in the formation of a white solid. The addition of H$_3$PO$_4$ was continued until no more white solid appeared to precipitate. The solid was filtered and washed with MTBE (100 mL). The product was recrystallized with MeOH/MTBE to provide 109 as the phosphate salt (0.4 g, 36%).

$^1$H-NMR (300 MHz, CD$_3$OD): δ 1.09-1.60 (m, 7H), 1.68-1.71 (m, 1H), 1.98-2.02 (m, 1H), 2.04-2.15 (m, 1H), 2.31 (s, 3H), 2.50-2.55 (m, 1H), 2.64-2.65 (m, 1H), 3.06-3.07 (m, 1H), 3.16 (br.s., 2H), 3.54-3.55 (m, 1H), 7.02-7.17 (m, 3H). $^{13}$C-NMR (75 MHz, CD$_3$OD): δ 20.2, 21.7, 25.8, 35.0, 35.8, 60.3, 125.8, 127.4, 128.0, 130.8, 137.2, 137.4. HPLC (method: 20 mm C18 RP column—gradient method 2-95% ACN/water/0.1% formic acid; Wavelength: 210 nm):-retention time: 2.51 min. purity: 97.7%. MS (M+H): 259.2.

Example 7. Synthesis of (+)-3-(Methyl-d$_3$)-17-(methyl-d$_3$)-(9α,13α,14α)-morphinan (110)

Compound 110 was prepared as outlined below. Details of the synthesis follow.

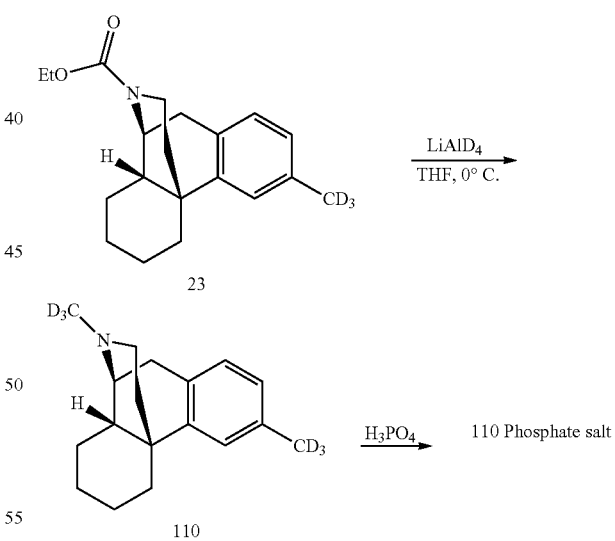

110

Synthesis of (+)-3-(methyl-d$_3$)-17-(methyl-d$_3$)-(9α, 13α,14α)-morphinan (110)

A mixture of 23 (2.5 g, 8 mmol, see Example 5) in THF (70 mL) was treated with LiAlD$_4$ (1.7 g, 32 mmol, Cambridge Isotopes, 98 atom % D) at 0° C. The mixture was allowed to warm to ambient temperature and was stirred overnight. Water (1 mL) was added to quench the reaction, followed by NaOH (24%, 10 mL). The mixture was stirred for 30 minutes, during which time white solid precipitated. The solid was filtered and the filtrate was concentrated under reduced pressure. The crude product was purified by preparative HPLC (see conditions described in Example 5) to provide 110. The free amine was dissolved in MTBE (50 mL) and was heated to reflux. $H_3PO_4$ (in isopropanol) was added dropwise, resulting in the formation of a white solid. The addition of $H_3PO_4$ was continued until no more white solid appeared to precipitate. The solid was filtered and washed with MTBE (100 mL) to provide 1.2 g of solid. The product was recrystallized in MeOH/MTBE to provide 110 as the phosphate salt (1 g, 36%).

$^1$H-NMR (300 MHz, $CD_3OD$): δ 1.09-1.13 (m, 1H), 1.24-1.33 (m, 1H), 1.39-1.72 (m, 6H), 1.95-2.04 (m, 1H), 2.16-2.18 (m, 1H), 2.50-2.54 (m, 1H), 2.60-2.68 (m, 1H), 3.07-3.16 (m. and s., 3H), 3.54-3.55 (m, 1H), 7.02-7.17 (m, 3H). $^{13}$C-NMR (75 MHz, $D_2O$): δ 21.4, 23.2, 25.5, 25.6, 34.7, 39.3, 43.0, 47.8, 60.4, 126.4, 127.5, 128.3, 131.2, 138.0. HPLC (method: 20 mm C18 RP column-gradient method 2-95% ACN/water/0.1% formic acid; Wavelength: 210 nm): retention time: 2.61 min., purity >99.9%. MS (M+H): 262.2.

Example 8. Evaluation of Metabolic Stability in CYP2D6 SUPERSOMES™

Human CYP2D6 SUPERSOMES™ were purchased from GenTest (Woburn, Mass., USA). 7.5 mM stock solutions of test compounds (Compounds 100, 102, 104, 106, dextromethorphan, a deuterated analog of dextromethorphan wherein each methyl group was replaced with $CD_3$ ("$d_6$-dextromethorphan", chemical name (+)-3-d3-methoxy-17-d3-methyl-(9α,13α,14α)-morphinan, also referred to as Compound 101 in U.S. Ser. No. 12/112,936, and as "Test Compound" in FIG. 1 and Table 2 below), the ethyl ether analog of dextromethorphan ("dextroethorphan") or the isopropyl ether analog of dextromethorphan ("dextroisopropor-phan")) were prepared in DMSO. The 7.5 mM stock solutions were diluted to 50 µM in acetonitrile (ACN). The 1000 pmol/mL CYP2D6 supersomes were diluted to 62.5 pmol/mL in 0.1 M potassium phosphate buffer, pH 7.4, containing 3 mM $MgCl_2$. The diluted SUPERSOMES™ were added to wells of a 96-well deep-well polypropylene plate in triplicate. 10 µL of the 50 µM test compound was added to the supersomes and the mixture was pre-warmed for 10 minutes. Reactions were initiated by addition of pre-warmed NADPH solution. The final reaction volume was 0.5 mL and contained 50 pmol/mL CYP2D6 SUPERSOMES™, 1 µM test compound, and 2 mM NADPH in 0.1 M potassium phosphate buffer, pH 7.4, and 3 mM $MgCl_2$. The reaction mixtures were incubated at 37° C. and 50 µL aliquots were removed at 0, 5, 10, 20, and 30 minutes and added to shallow-well 96-well plates which contained 50 µL of ice-cold ACN with internal standard to stop the reactions. The plates were stored at 4° C. for 20 minutes after which 100 µL of water was added to the wells of the plate before centrifugation to pellet precipitated proteins. Supernatants were transferred to another 96-well plate and analyzed for amounts of parent remaining by LC-MS/MS using an Applied Bio-systems API 4000 mass spectrometer.

The in vitro half-life ($t_{1/2}$) for each of the test compounds was calculated from the slopes of the linear regression of % parent remaining (ln) vs incubation time relationship: in vitro $t_{1/2}$=0.693/k, where k=−[slope of linear regression of % parent remaining(ln) vs incubation time]. Data analysis was performed using Microsoft Excel Software.

FIG. 1 and Table 2, below, show the results of the SUPERSOMES™ experiment. Note that in FIG. 1, the curves for Compounds 100 and 104 overlap one another. "Test Compound" in FIG. 1 and Table 2 refers to deuterated dextromethorphan ("$d_6$-dextromethorphan", (+)-3-d3-methoxy-17-d3-methyl-(9α,13α,14α)-morphinan, which is also referred to as Compound 101 in U.S. Ser. No. 12/112,936, incorporated by reference herein).

TABLE 2

Calculated Half-life in SUPERSOMES ™.

| Compound | $t_{1/2}$ ± SD (min) |
| --- | --- |
| Dextromethorphan | 1.7 ± 0.3 |
| Test Compound | 5.6 ± 1.5 |
| Dextroethorphan | 10.3 ± 2.1 |
| Dextroisoproporphan | 21.7 ± 1.6 |
| Compound 106 | 36.0 ± 2.8 |
| Compound 102 | 39.0 ± 1.9 |
| Compound 104 | 49.1 ± 4.1 |
| Compound 100 | 51.3 ± 3.7 |

Each of the deuterated compounds tested demonstrated a longer half-life when incubated with CYP2D6 SUPERSOMES™ than any of the corresponding undeuterated test compounds or a deuterated version of dextromethorphan (Test Compound). Thus, in this assay, the compounds of this invention were more resistant to metabolism than dextromethorphan or deuterated dextromethorphan (Test Compound).

Example 9. Determination of Metabolic Stability of Test Compounds Using Human Liver Microsomes Human liver microsomes (20 mg/mL) were obtained from Xenotech, LLC (Lenexa, Kans.). β-nicotinamide adenine dinucleotide phosphate, reduced form (NADPH), magnesium chloride ($MgCl_2$), and dimethyl sulfoxide (DMSO) were purchased from Sigma-Aldrich.

7.5 mM stock solutions of test compounds were prepared in DMSO. The 7.5 mM stock solutions were diluted to 50 µM in acetonitrile (ACN). The 20 mg/mL human liver microsomes were diluted to 1.25 mg/mL (1 mg/mL final) in 0.1 M potassium phosphate buffer, pH 7.4, containing 3 mM $MgCl_2$. The diluted microsomes (375 µL) were added to wells of a 96-well polypropylene plate in triplicate. 10 µL of the 50 µM test compound was added to the microsomes and the mixture was pre-warmed for 10 minutes. Reactions were initiated by addition of 125 µL of pre-warmed NADPH solution. The final reaction volume was 0.5 mL and contained 1.0 mg/mL human liver microsomes, 1 µM test compound, and 2 mM NADPH in 0.1 M potassium phosphate buffer, pH 7.4, and 3 mM $MgCl_2$. The reaction mixtures were incubated at 37° C., and 50 µL aliquots were removed at 0, 5, 10, 20, and 30 minutes and added to shallow 96-well plates which contained 50 µL of ice-cold ACN with internal standard to stop the reactions. The plates were stored at 4° C. for 20 minutes after which 100 µL of water was added to the wells of the plate before centrifugation to pellet precipitated proteins. Supernatants were transferred to another 96-well plate and analyzed for amounts of parent remaining by LC-MS/MS using an Applied Bio-systems API 4000 mass spectrometer.

7-ethoxy coumarin was used as a positive control.

The in vitro $t_{1/2}$s for test compounds were calculated from the slopes of the linear regression of % parent remaining (ln) vs incubation time relationship:

in vitro $t_{1/2}=0.693/k$, where k=−[slope of linear regression of % parent remaining(ln) vs incubation time]

Data Analysis was Performed Using Microsoft Excel Software.

Figure 2:
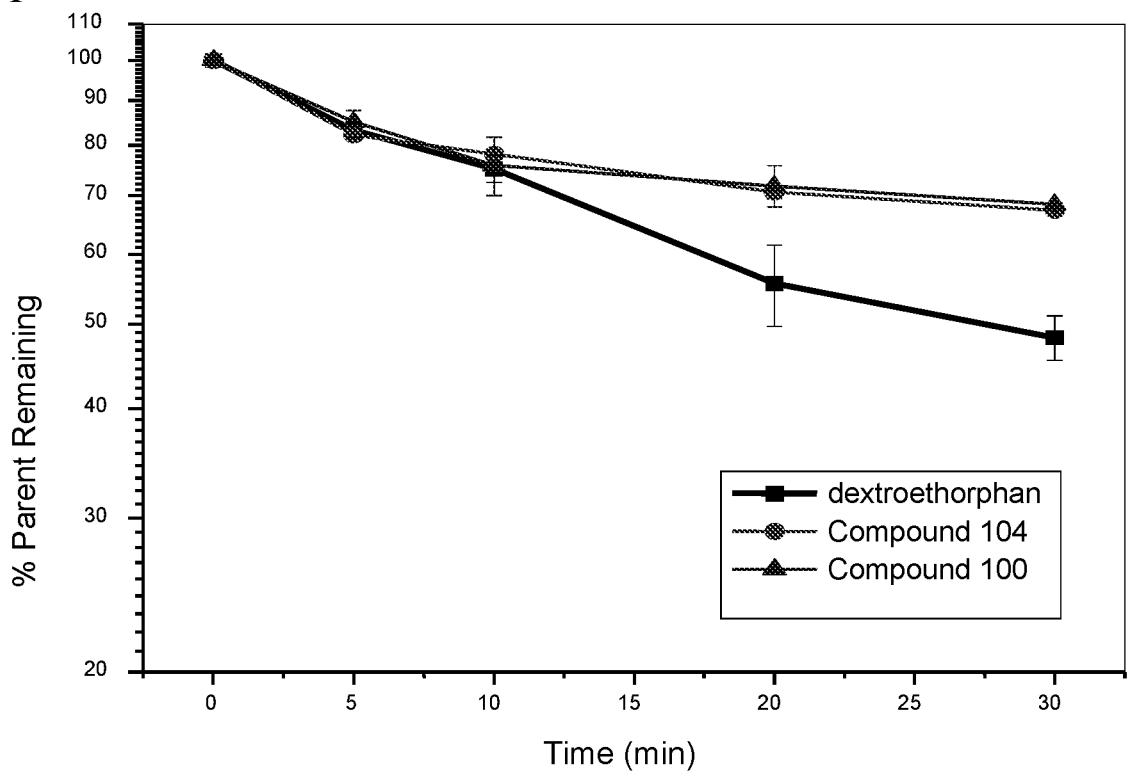
FIG. 2, panels A and B, depict the metabolic stability of dextroethorphan (panel A), dextroisoproporphan (panel B), and compounds of this invention in human liver microsomes.
Figure 2:
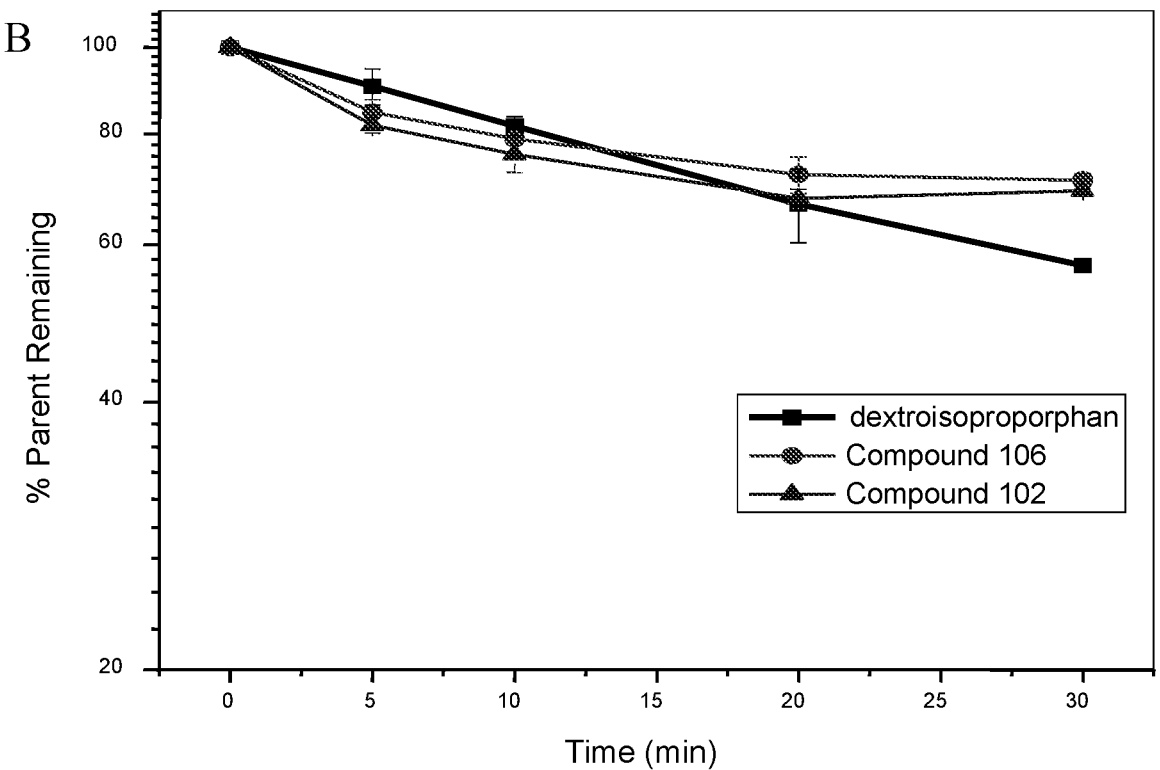
Figure 3:
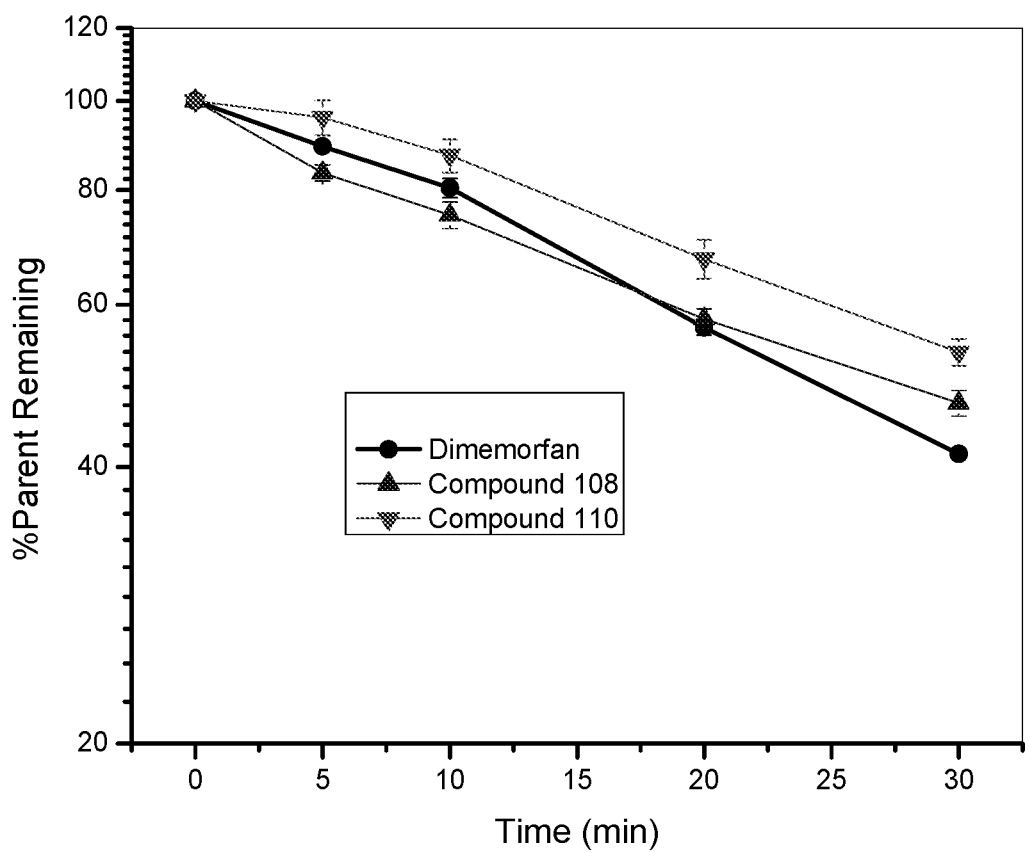
FIG. 3 depicts the metabolic stability of dimemorfan and of compounds of this invention in human liver microsomes.

FIG. 2 (panels A and B), FIG. 3, Table 3, and Table 4 show the results of this experiment.

TABLE 3

Calculated Half-life in Human Liver Microsomes

| Compound | $t_{1/2}$ ± SD (min) | Change over non-deuterated compound |
|---|---|---|
| Dextroethorphan | 28.3 ± 0.6 | n/a |
| Compound 104 | 59.1 ± 2.2 | 109% |
| Compound 100 | 59.2 ± 1.7 | 109% |
| Dextroisoproporphan | 36.1 ± 1.6 | n/a |
| Compound 106 | 68.8 ± 0.9 | 91% |
| Compound 102 | 61.0 ± 0.4 | 69% |

In the case of both dextroethorphan and dextroisoproporphan, deuteration of the alkyl ether ($R^1$) resulted in a significant increase in half life ($t_{1/2}$) in human liver microsomes as compared to the undeuterated counterpart.

TABLE 4

Calculated Half-life in Human Liver Microsomes

| Compound | Ave. $t_{1/2}$ (n = 2) | Change over non-deuterated compound |
|---|---|---|
| Dimemorfan | 23.1 | n/a |
| Compound 108 | 28.0 | 21% |
| Compound 110 | 31.6 | 37% |

In the case of dimemorfan, deuteration of $R^1$ resulted in a significant increase in half life ($t_{1/2}$) in human liver microsomes as compared to the undeuterated counterpart. Deuteration of the N-methyl moiety ($R^2$) caused a further significant increase in $t_{1/2}$.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

We claim:

1. A pharmaceutically acceptable salt of a compound represented by the following structural formula:

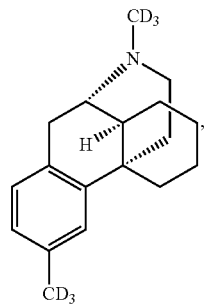

Compound 110 wherein the pharmaceutically acceptable salt is selected from sulfate, pyrosulfate, bisulfate, sulfite, bisulfate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, 3-hydroxybutyrate, glycolate, maleate, tartrate, methanesulfonate, propanesulfonate, naphthalene-1-sulfonate, naphthalene-2-sulfonate, and mandelate.

2. The pharmaceutically acceptable salt of claim 1, wherein the salt is selected from chloride, bromide, and phosphate.

3. The pharmaceutically acceptable salt of claim 1, wherein the salt is phosphate.

4. The pharmaceutically acceptable salt of claim 1, wherein the deuterium incorporation at each designated deuterium atom is at least 90%.

5. The pharmaceutically acceptable salt of claim 1, wherein the deuterium incorporation at each designated deuterium atom is at least 95%.

6. The pharmaceutically acceptable salt of claim 1, wherein the deuterium incorporation at each designated deuterium atom is at least 97%.

7. A pharmaceutical composition comprising the pharmaceutically acceptable salt of claim 1 and a pharmaceutically acceptable carrier.

8. The pharmaceutical composition of claim 7, further comprising a second therapeutic agent selected from quinidine, quinidine sulfate, oxycodone, and gabapentin.

9. The pharmaceutical composition of claim 7, wherein the amount of the pharmaceutically acceptable salt of the compound is in the range from 4 mg to 350 mg.

10. The pharmaceutical composition of claim 7, wherein the amount of the pharmaceutically acceptable salt of the compound is in the range from 10 mg to 90 mg.

11. A method of treating a subject suffering from a disease or condition selected from emotional lability; pseudobulbar affect; autism; neurological disorders and neurodegenerative diseases; brain injuries; disturbances of consciousness disorders; cardiovascular diseases; glaucoma; tardive dyskinesia; cancer; rheumatoid arthritis; diabetic neuropathy; retinopathic diseases; diseases or disorders caused by homocysteine-induced apoptosis; diseases or disorders caused by elevated levels of homocysteine; chronic pain; intractable pain; neuropathic pain, sympathetically mediated pain; pain associated with gastrointestinal dysfunction; mouth pain; back pain; central pain syndrome; complex regional pain syndrome; epileptic seizures; epileptic hemiplegia; acquired epileptiform aphasia (Landau-Kleffner syndrome); severe myoclonic epilepsy of infancy (SMEI); early infantile epileptic encephalopathy; post-stroke seizure; febrile seizures; post-traumatic seizures; tinnitus; sexual dysfunction; intractable coughing; dermatitis; addiction disorders; Rett syndrome (RTT); voice disorders due to uncontrolled laryngeal muscle spasms; methotrexate neurotoxicity; and fatigue caused by cancer; comprising the step of administering to a subject in need thereof a therapeutically effective amount of the pharmaceutically acceptable salt of claim 1.

12. The method of claim 11, wherein the salt is selected from chloride, bromide, and phosphate.

13. The method of claim 11, wherein the salt is phosphate.

14. The method of claim 11, wherein the deuterium incorporation at each designated deuterium atom is at least 90%.

15. The method of claim 11, wherein the deuterium incorporation at each designated deuterium atom is at least 95%.

16. The method of claim 11, wherein the deuterium incorporation at each designated deuterium atom is at least 97%.

17. The method of claim 11, wherein the disease or condition is epileptic seizures.

18. The method of claim 17, wherein the epileptic seizures are generalized epileptic seizures or partial epileptic seizures.

19. The method of claim 11, wherein the disease or condition is severe myoclonic epilepsy of infancy (SMEI), early infantile epileptic encephalopathy, post-stroke seizures, febrile seizures, or post-traumatic seizures.

20. The method of claim 11, wherein the amount of the compound administered is in the range from 4 mg to 350 mg.

21. The method of claim 11, wherein the amount of the compound administered is in the range from 10 mg to 90 mg.

22. The method of claim 11, further comprising the step of co-administering to the subject a second therapeutic agent selected from quinidine, quinidine sulfate, oxycodone, and gabapentin.

* * * * *